United States Patent [19]

Brook et al.

[11] Patent Number: 5,068,800

[45] Date of Patent: * Nov. 26, 1991

[54] CRACK DETECTION METHOD FOR SHAFT AT REST

[75] Inventors: Warren R. Brook, Medford, N.J.; William H. Miller, Loudonville, N.Y.

[73] Assignee: REM Technologies, Inc., Albany, N.Y.

[*] Notice: The portion of the term of this patent subsequent to Dec. 4, 2007 has been disclaimed.

[21] Appl. No.: 584,893

[22] Filed: Sep. 19, 1990

Related U.S. Application Data

[63] Continuation-in-part of Ser. No. 323,313, Mar. 14, 1989, Pat. No. 4,975,855.

[51] Int. Cl.$^5$ .................... G01N 27/82; G01R 33/12
[52] U.S. Cl. ...................... 364/507; 364/551.02; 73/581; 73/622; 340/680
[58] Field of Search .......... 364/507, 508, 550, 551.02; 340/679, 680, 683; 73/579, 581, 659, 660, 622

[56] References Cited

U.S. PATENT DOCUMENTS

| | | | |
|---|---|---|---|
| 3,411,344 | 11/1968 | Lloyd | 73/579 |
| 4,195,528 | 4/1980 | Takahashi | 73/579 |
| 4,342,229 | 8/1982 | Massa | 73/579 |
| 4,380,172 | 4/1983 | Imam et al. | 73/659 |
| 4,408,294 | 10/1983 | Imam et al. | 364/508 |
| 4,559,600 | 12/1985 | Rao | 364/474 |
| 4,628,261 | 12/1986 | Huschelrath et al. | 364/507 |
| 4,685,335 | 8/1987 | Sato et al. | 73/660 |
| 4,689,993 | 9/1987 | Slettemoen | 73/579 |
| 4,750,134 | 6/1988 | Huschelrath et al. | 364/508 |
| 4,751,461 | 6/1988 | McWhirter et al. | 364/507 |
| 4,751,657 | 6/1988 | Imam et al. | 364/508 |
| 4,764,970 | 8/1988 | Hayashi et al. | 364/507 |
| 4,803,639 | 2/1989 | Steele et al. | 364/507 |
| 4,805,457 | 2/1989 | Oates et al. | 73/572 |
| 4,817,016 | 3/1989 | Thompson et al. | 364/507 |
| 4,821,204 | 4/1989 | Huschelrath | 364/481 |
| 4,896,278 | 1/1990 | Grove | 364/507 |
| 4,897,796 | 1/1990 | Salvado | 364/507 |
| 4,918,616 | 4/1990 | Yoshimura et al. | 364/507 |
| 4,975,855 | 12/1990 | Miller et al. | 364/507 |

OTHER PUBLICATIONS

"The Vibrational Behavior of a Turbine Rotor Containing a Transverse Crack", B. Grabowski, Transactions of the ASME, vol. 102, Jan. 1980.

Primary Examiner—Parshotam S. Lall
Assistant Examiner—Brian M. Mattson
Attorney, Agent, or Firm—Heslin & Rothenberg

[57] ABSTRACT

The presence, size and location of a crack in a shaft is determined by comparing actual measured natural frequencies of the shaft system with the results of an analytical model. From a multi-station analytical model of an uncracked shaft system, natural frequencies and associated mode shapes are derived. A suspected axial location of a crack is defined, and a natural frequency of interest is selected which has an associated mode shape exhibiting significant localized bending at the suspected axial location of the crack and at a site of response measurement. The analytical model is modified to include a representation of an asymmetric crack at the suspected crack location, and a predicted split and downward shift of a lateral natural frequency of interest and/or a predicted downward shift of a torsional natural frequency of interest as a function of crack depth is calculated from the modified model. The actual shaft system is subjected to an excitation force, and vibrational response measurements are taken. A fast Fourier transform analyzer derives a frequency response function from the measurements which indicates the actual natural frequencies of the shaft system. A comparison of actual natural frequency(s) in the region near the natural frequency of interest with frequency values predicted by the modified model is employed to determine the presence and severity of a crack in the shaft.

46 Claims, 21 Drawing Sheets

CRACK DETECTION METHOD FOR SHAFT AT REST

GOVERNMENT RIGHTS

Certain features of this invention were made with Government support under Contract NRC-04-86-130 awarded by the U.S. Nuclear Regulatory Commission. The Government has certain rights in such features of the invention.

RELATED APPLICATION

This application is a continuation-in-part of application Ser. No. 07/323,313, filed Mar. 14, 1989, now U.S. Pat. No. 4,975,855 issued on Dec. 4, 1990.

BACKGROUND OF THE INVENTION

This invention relates in general to the field of non-destructive testing and more particularly to a method for determining the presence, size and location of a crack in a shaft. For purposes of this description, a crack is defined as any non-designed physical discontinuity, and the term shaft encompasses any axially extending structure which has a length considerably larger than its cross sectional dimension and is subject to time varying forces. Such structures take a wide variety of forms including, traditionally, motor rotors, shafts of pumps, generators, compressors and turbines, bolts and other fasteners, piping, etc. and, for purposes of this invention, such forms as aircraft fuselages, aircraft wings, and ship hulls. Although the present invention is applicable to any such structures, it will be presented, by way of example, primarily in the context of detecting a crack in a reactor coolant pump shaft of a pressurized water reactor (PWR).

Nuclear reactors have been operating and producing useful electricity for many years. Within the last few years, several plants have found cracks in the reactor coolant pump shaft near the thermal barrier.

The large reactor coolant pump of a PWR circulates water out of the reactor vessel into steam generators which in turn pass steam to a steam turbine. The reactor coolant pump system consists of a vertical pump with a vertical motor mounted on the pump from above. In a typical design, the entire shaft system hangs vertically and is supported by a thrust bearing located on the top of the vertical motor. The pump system usually has an overhung impeller and an axial suction inlet from below the pump. The cooling water exits the pump through a single radial discharge in the horizontal direction. A net radial force is developed on the rotating shaft during the operation of the pump. This unidirectional unbalanced force applied to the rotating pump shaft can lead to a fatigue crack in the shaft and subsequent pump shaft failure.

The consequences of an unforeseen pump shaft failure can be dire. A nuclear facility can lose millions of dollars a day in revenues from an unscheduled outage. Further, these pumps are responsible for cooling the reactor, so a failure might lead to a potential melt-down situation and the associated radiation hazard. Since pump shaft replacement is an expensive, time consuming project, it is highly desirable to be able to discover the crack condition early and thus have time to plan and schedule the replacement.

A reliable, early warning method for the identification of shaft cracks, which is relatively easy to implement, is not presently available. Existing devices typically collect and analyze vibrational data off a running machine. However, operating vibrational data in the form of $1\times$ (operating speed) and $2\times$ (twice operating speed) amplitude and phase data is usually clouded with electrical, mechanical and background noise such that little useful information relative to the shaft condition can be obtained.

Field studies show that with existing measurement equipment, cracks are not recognizable until they reach a depth of at least 20% of the shaft diameter. The inability to detect a crack at earlier stages can leave insufficient time to schedule the manpower, parts, etc. required to replace the shaft.

A critical need thus exists for a reliable, easy to implement shaft crack detection method which can identify the presence, size, and location of a shaft crack in the early stages of crack development. The test method has to be applied on-site, in a non-destructive fashion, and with minimal radiation exposure to the test personnel. Further complicating the situation is the fact that only limited access to the reactor coolant pump shaft is available.

SUMMARY OF THE INVENTION

This need is satisfied and the deficiencies of the prior art overcome, in accordance with the principles of the present invention through the application of a modal analysis test method. By taking advantage of the amplification associated with natural frequencies of the shaft, the new test method is able to identify the presence of a crack having a radial depth on the order of 5% of the pump shaft diameter in the region of the crack. This provides a significantly earlier warning of impending shaft failure than existing techniques allowing for a planned replacement during a scheduled outage. The new method when utilized to monitor the shaft for crack initiation and subsequent propagation will enable nuclear power plant operators to avoid difficult shut-down situations and costly unscheduled outages. The test can be applied with the shaft at rest, thus avoiding the background noise problems associated with running machine data. Further, the method allows both the external excitation to the shaft and the response to be obtained through the existing motor stand access holes, without any disassembly, and yet is capable of detecting a crack located anywhere along the axis of the shaft.

The method of the present invention utilizes an analytical model of the shaft system under test to guide and interpret the results of a vibrational test applied to the actual shaft system. In the vibrational test, the shaft system's response to a force excitation is measured along a radial direction for lateral analysis and/or along a tangential direction for torsional analysis. A correlation between the actual natural frequency(s) exhibited by the shaft system in response to the force excitation, and a predicted split and shift in a lateral analysis natural frequency of interest and/or a predicted downward shift in a torsional analysis natural frequency of interest provided by the analytical model, is used to identify the presence and severity of a crack in the shaft.

In accordance with one aspect of the present invention, a multi-station structural dynamics model of an uncracked shaft system is employed to derive lateral analysis and/or torsional analysis natural frequencies and associated mode shapes. A probable or suspected axial location of a crack is determined, and a natural frequency of interest for lateral and/or torsional analysis is selected having a mode shape which exhibits significant localized bending at the probable axial location of the crack and a site of response measurement. The model is then modified to incorporate a representation of an asymmetric crack at the probable axial location, and the resultant split and shift of a lateral analysis natural frequency of interest and/or shift in a torsional analysis natural frequency of interest as a function of crack depth is determined. An excitation force is introduced at the excitation site on a shaft system under test, and measurements are taken of the shaft system vibrational response along multiple radial directions for lateral analysis and/or a tangential direction for torsional analysis. The measurements are processed, preferably by a fast Fourier transform analyzer, to determine the actual natural frequency(s) of the shaft system in the region of the frequency of interest. A correlation between the actual natural frequency(s) and the shift and split in the lateral analysis natural frequency of interest and/or the shift in the torsional analysis natural frequency of interest predicted by the analytical model provides an indication of shaft crack presence and severity.

In a further aspect of the invention, the crack is modeled by determining an equivalent diameter and effective length of a right circular section for a stiff axis extending substantially parallel to the crack wave front and a soft axis extending along the depth of the crack for lateral analysis, and for a polar axis extending longitudinally through the center of the shaft for torsional analysis. In another aspect of the invention, the analytical model of the shaft system can optionally be verified by applying a roving modal analysis to a physical model of the shaft system. In a further aspect of the invention, the circumferential location of the crack can be determined by analyzing the lateral analysis frequency response function of the shaft system along multiple radial directions.

The test method of the present invention may be advantageously implemented in a lateral analysis mode and/or a torsional analysis mode. The latter requires only a single vibrational response measurement to determine the presence and depth of a crack; the former further affords an indication of the circumferential location of a shaft crack. The invention also contemplates independent or integrated application of the analytical and experimental portions of the modal analysis method.

BRIEF DESCRIPTION OF THE DRAWINGS

These and other objects, features and advantages of the invention will be more readily understood from the following detailed description when read in conjunction with the accompanying drawings, in which:

FIG. 18b is a plot of an actual coherence function for the frequency response function of FIG. 18a;

FIG. 18c is a plot of an expanded region of the frequency response function of FIG. 18a;

DETAILED DESCRIPTION

Figure 1:
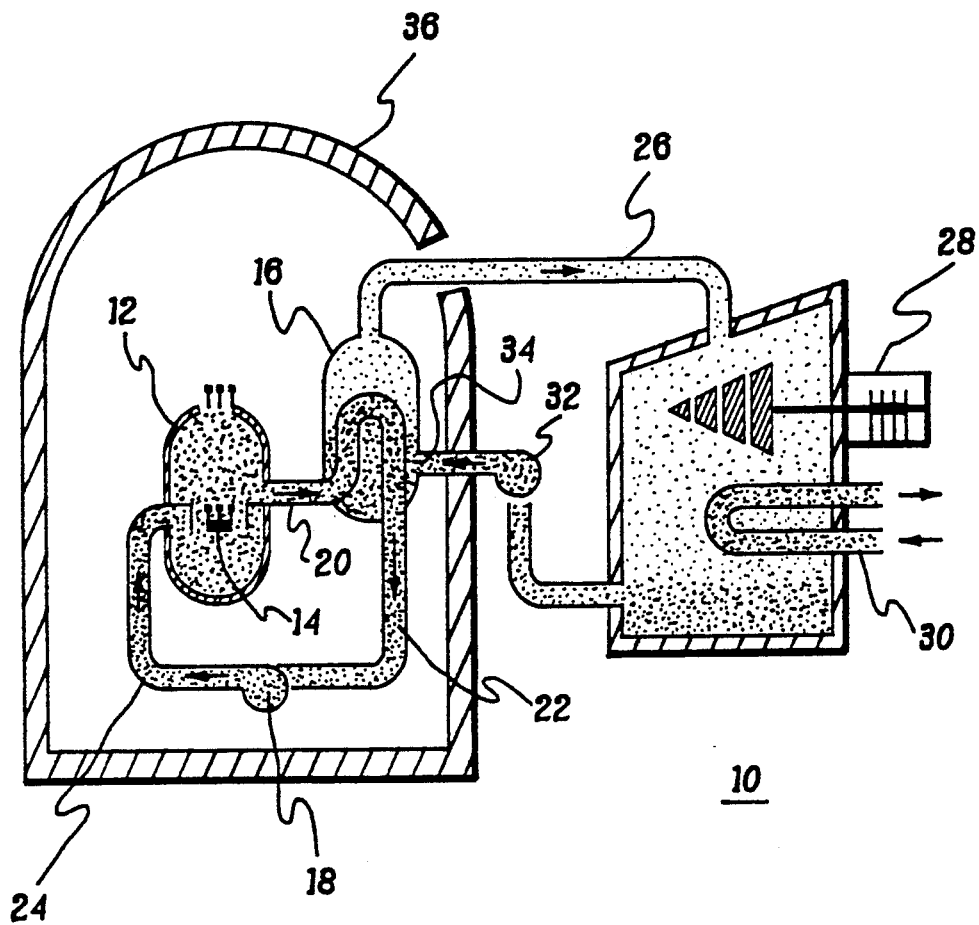
FIG. 1 is a simplified schematic representation of a typical pressurized water reactor (PWR) nuclear power plant.

A schematic of a typical pressurized water reactor (PWR) nuclear power plant 10 is shown in FIG. 1. In operation, high temperature, high pressure water is pumped from the reactor vessel 12 (from around the reactor core 14) to a steam generator (heat exchanger) 16 by the reactor coolant pump 18. A continuous loop of piping 20, 22, 24 interconnects the pressure vessel 12, steam generator 16 and reactor coolant pump 18, as shown. Steam generator 16 in turn passes steam along steam line 26 to a steam turbine generator 28. Finally, cooling water from a condenser 30 is pumped by pump 32 into the inlet 34 of steam generator 16.

Figure 2:
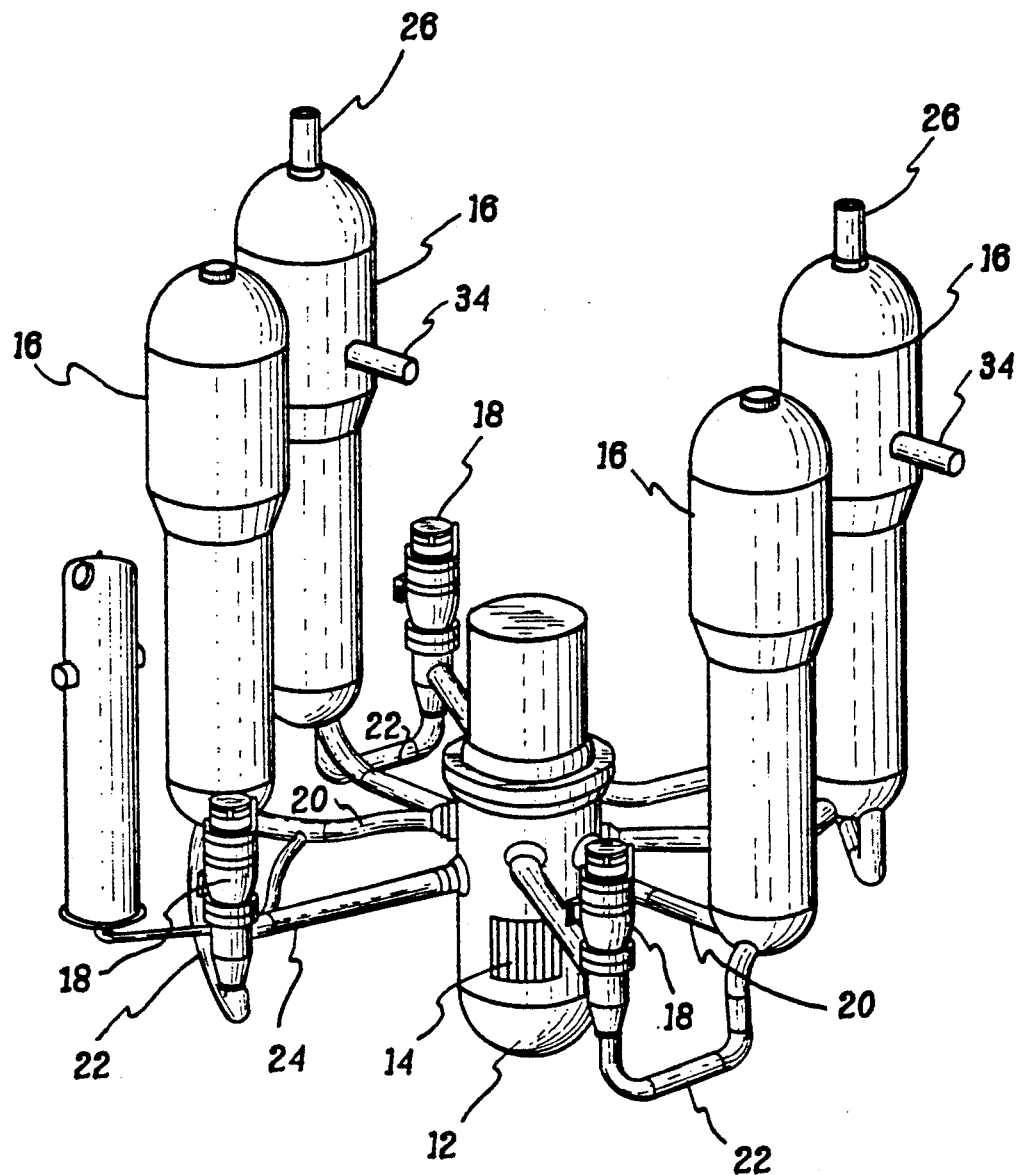
FIG. 2 is a more detailed illustration of a reactor coolant system for a PWR.

FIG. 2 is a more detailed sketch of the reactor coolant system for the PWR which is housed inside the containment structure 36 (FIG. 1). Four reactor coolant pumps (RCPs) 18 and associated steam generators 16 surround and are interconnected with the reactor vessel 10 12. If one of the RCPs 18 should fail and be shut down because of a crack in the pump shaft, the nuclear power plant may still be able to operate but obviously at a reduced load and with significantly reduced revenue generated. The present invention relates to an early warning method for detecting shaft cracks which will enable plant operators to avoid unscheduled outages.

Figure 3:
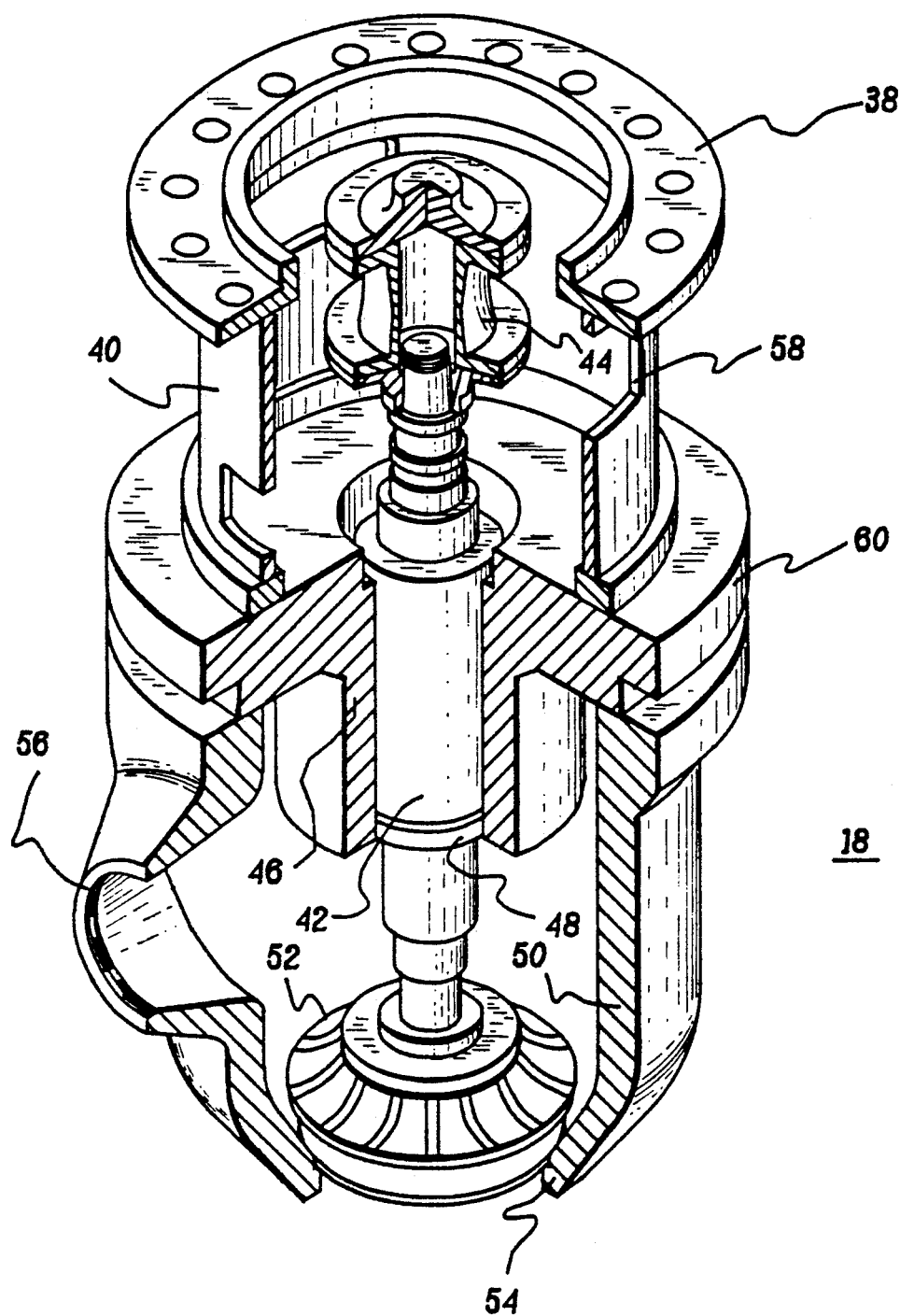
FIG. 3 is a partially broken away sectional view of a reactor coolant pump.
Figure 4:
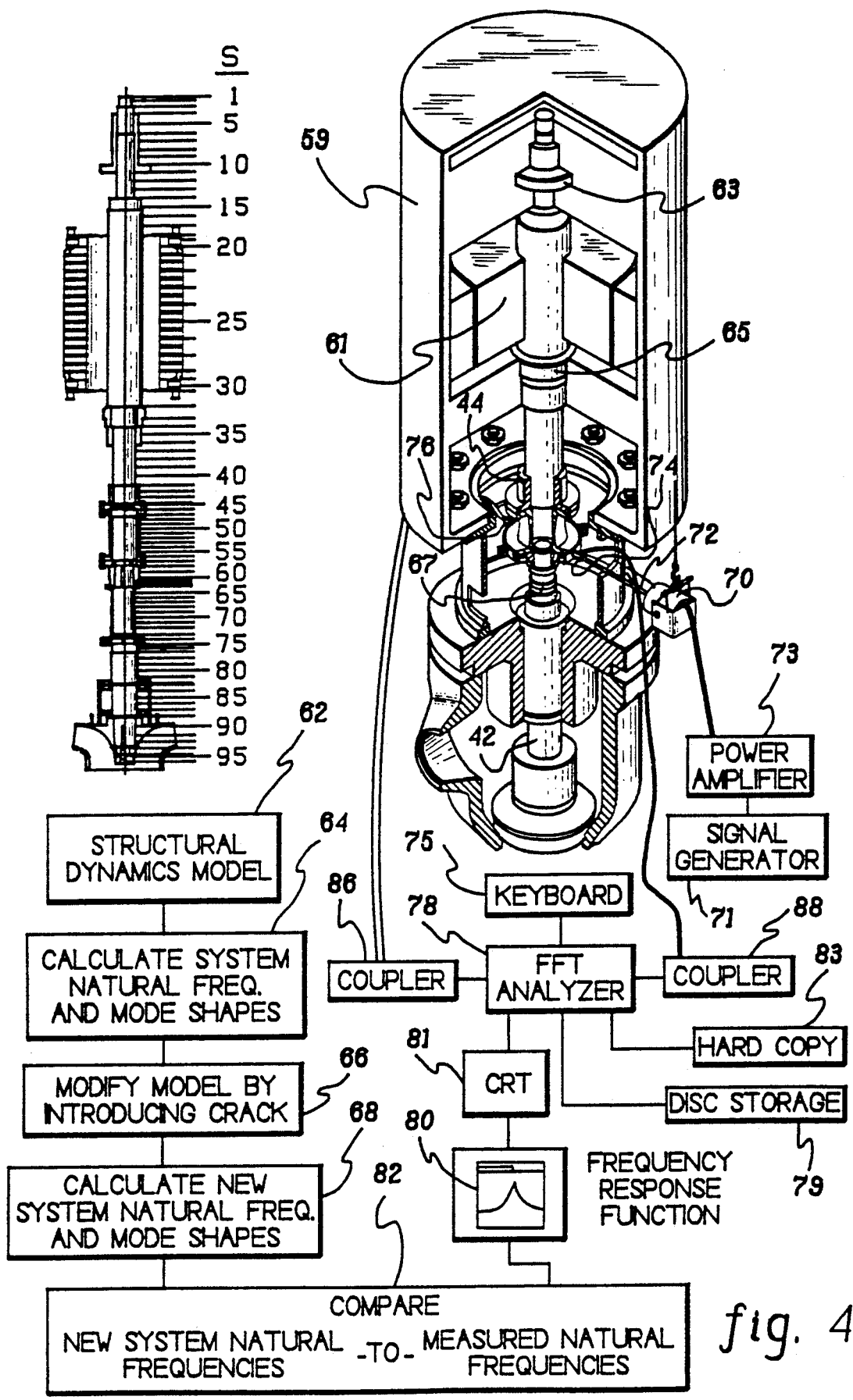
FIG. 4 is schematic depiction, partly in block diagram form, of the general modal analysis test method of the present invention.

FIG. 3 is a sectional, partially broken away view of a typical reactor coolant pump 18. A drive motor is mounted on flange 38 atop motor support housing 40. The motor's rotor is connected to the pump shaft 42 by a spool piece coupling 44. Drive motor 59, motor rotor 61 and motor bearings 63 and 65 are shown in FIG. 4.

Referring again to FIG. 3, a radial guide bearing 46 surrounds a portion of pump shaft 42 at a location above a thermal barrier 48. Thermal barrier 48 serves to isolate the bearing area from the extremely high temperatures of the water within casing 50. An impeller 52 is mounted at the lower end of shaft 42 by a set of bolts (not shown).

Water from the steam generator enters vertically upward into the suction nozzle 54 of the reactor coolant pump 18. The pump discharge is horizontal through discharge nozzle 56 into the reactor vessel. During operation of the pump, discharge flow causes a net pressure differential across the pump shaft 42. Since the pump shaft is rotating in the pump casing 50, a given point on the shaft is subjected to a cyclic force. This force is reacted by the pump shaft 42 on the guide bearing 46. Generally the thermal barrier and the guide bearing journal have a sleeve shrunk on the shaft at these locations. In some cases, the sleeve is further secured through the use of a shear pin, or welding, or both locking mechanisms (not shown). The shear pin and welding give rise to stress concentrations which in combination with the cyclic force can result in the formation of a shaft crack, often just below the thermal barrier. Continued operation of the pump will cause the crack to propagate. Shaft cracks have occurred in operating nuclear power plants and have apparently gone undetected until the pump impeller 52 broke off the shaft 42.

The new modal test method of the present invention can be advantageously employed to identify the presence, size and location of a crack in a vertical reactor coolant pump shaft or shaft system. The method recognizes that the only access to the shaft system is through the cutouts 58 in the motor support housing 40 which is mounted on the main flange 60 and encloses the coupling 44. No other access to the pump shaft 42 is readily available. The method of the present invention enables both the excitation to the shaft system and the response to be obtained through the motor stand access holes 58 without any disassembly.

FIG. 4 presents an overview of the modal analysis test method of the present invention as it might be applied to the detection of cracks in a RCP shaft. As shown, a multi-station structural dynamics or analytical model 62 of the shaft system, with an uncracked shaft, is developed. From this model, the shaft system's lateral and/or torsional natural frequencies and associated mode shapes are calculated (box 64). The model is then modified by introducing a representation of a crack at a suspected or probable axial location along the shaft (box 66). From the modified model, new system lateral and/or torsional natural frequencies and mode shapes are calculated (box 68). The new lateral natural frequencies reflect a shift and split of the original natural frequencies caused by the introduction of the crack. The new torsional natural frequencies reflect a downward shift of the original natural frequencies caused by the introduction of the crack.

Actual or measured natural frequencies of the shaft system are determined by introducing a force excitation (lateral and/or torsional) to the stationary pump shaft 42 from electromagnetic shaker 70 through a "stinger" 72 and load cell 74. Shaker 70 is driven by an input excitation signal provided by signal generator 71 through power amplifier 73. The vibrational response of the shaft system to the force excitation is measured by an accelerometer 76. Both the excitation and measured response are obtained through the access holes in the motor support housing. Response readings are taken along multiple radial directions for the lateral test and/or along a single offset tangential direction for the torsional test and then processed by a fast Fourier transform (FFT) analyzer 78. An input keyboard 75, disc storage device 79, CRT monitor 81 and hard copy printer 83 can be advantageously connected to FFT analyzer 78. The analyzer provides a frequency response function (FRF) 80, the peaks of which identify the measured lateral and/or torsional natural frequencies of the actual shaft system. A comparison of these measured lateral and/or torsional natural frequencies with the new system lateral and/or torsional natural frequencies calculated from the modified analytical model is used to determine the presence and severity of a crack in the shaft 42 (box 82).

The method of the present invention can be applied to the RCP shaft system while the shaft 42 is at rest. This avoids complications arising from background noise produced by operation of the system. The analytical model identifies a natural frequency of interest based on the axial locations of the suspected crack and the response measurement site of the shaft system. The modified model further predicts crack effect (split and shift) upon the lateral natural frequency of interest and/or crack effect (shift) upon the torsional natural frequency of interest as a function of crack depth. The analytical model thus serves as a road map for guiding the analysis of the actual vibrational test results. Further details and aspects of the method of the present invention will now be described in connection with the remaining drawing figures.

The method of this invention is based on the observation that there is a direct correlation between the existence of a crack and the crack's effect on the shaft system's lateral and torsional natural frequencies. A given shaft system will have a series of natural or resonant frequencies. If an asymmetric crack is introduced into the shaft, each of the lateral natural frequencies splits into two new, different lower frequencies. The lowest of the new frequencies is associated with a soft axis which extends along the depth of the crack; the other new frequency is associated with a stiff axis substantially parallel to the wave front of the crack. The reduction in value of lateral natural frequency and the separation between the two new frequencies can be correlated with the depth of the crack. The lateral natural frequency most affected by the modeled crack correlates to the axial location of the crack. The circumferential position of the crack can be determined by taking readings in multiple radial directions.

When an asymmetric crack is introduced into the shaft, each of the torsional natural frequencies shifts to a different lower frequency. The reduction in value of torsional natural frequencies can be correlated with the depth of the crack. The torsional natural frequency most affected by the modeled crack correlates to the axial location of the crack.

The modal analysis crack detection method of the present invention begins with an accurate multi-station analytical model of the shaft system (i.e. entire rotatable structure) under test. The analytical model should contain sufficient stations to ensure that the lateral and/or torsional natural frequencies of the shaft system can be calculated with a high degree of precision. Preferably, the accuracy provided by such a refined or enhanced model should be comparable to the frequency resolution of the FFT analyzer used in the experimental instrumentation of the shaft system. The inventors have discovered that a modeling criteria in which the separation between stations is no greater than one half of the local shaft system radius is desirable.

Figure 5A:
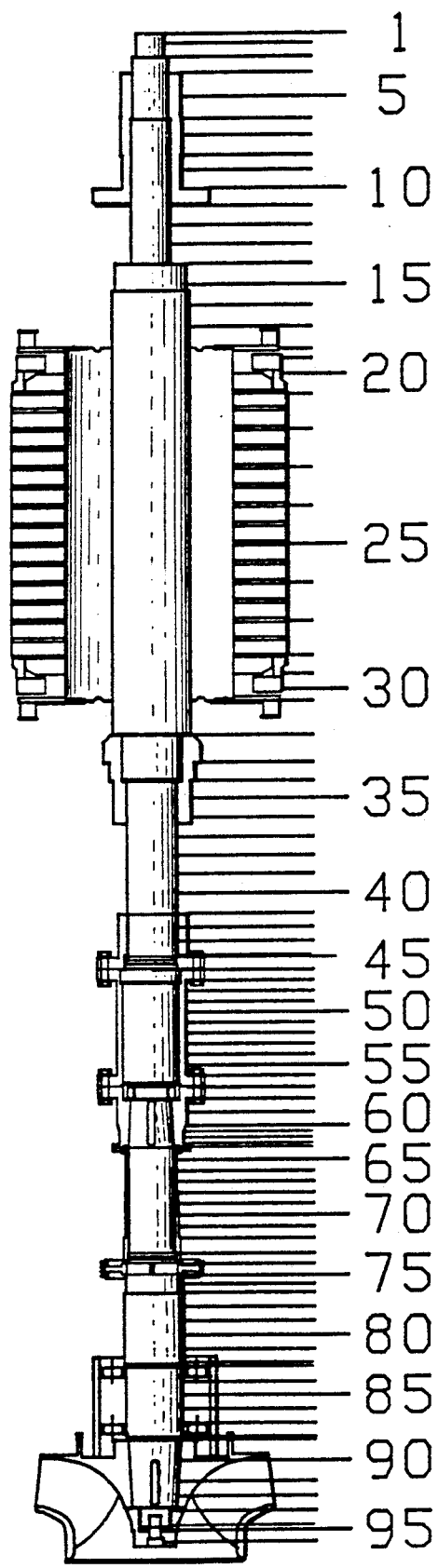
FIG. 5a is a graphical depiction of a multi-station structural dynamics model of a pump shaft system.

FIG. 5a graphically depicts multiple stations S1–S95 which might be used to model a RCP shaft system. The model includes a representation of the rotatable structural elements of the corresponding shaft system under test. Various rotor dynamics computer programs are publicly available and can be used to model the uncracked shaft or shaft system of such pumps. Refer, for example, to "DYNAMICS OF DISTRIBUTED PARAMETER ROTOR SYSTEMS: TRANSFER MATRIX AND FINITE ELEMENT TECHNIQUES", a doctoral thesis by R. L. Ruhl, dated January, 1970 and available from University Microfilms, Inc. of Ann Arbor, Mich. as document number 70-12,646; "THE EFFECT OF DISC FLEXIBILITY ON ROTOR DYNAMICS", a doctoral thesis of J. A. Dopkin, dated October 1972 and available from University Microfilms as document number 73-4739; NASA Report No. TN D-7385 "FORTRAN IV COMPUTER PROGRAM FOR CALCULATING CRITICAL SPEEDS OF ROTATING SHAFTS" by R. J. Trivisonno, dated August 1973; and/or CADENCE software available from Mechanical Technologies, Inc. of Albany, N.Y.

From such computer program models, the natural frequencies and associated mode shapes of the shaft system under test for lateral and/or torsional analysis can be derived, in known fashion. If desired, a physical model or sample of the shaft system under study can be subjected to a roving force modal analysis test to refine and/or verify the computer model predicted natural frequencies and mode shapes.

A suspected or probable axial location of a crack in the shaft under test is then defined. This location is obviously dependent upon the physical forces affecting the shaft in a particular application. As earlier indicated, in a RCP, the expected crack location is in the vicinity of the thermal barrier. A natural frequency of interest (lateral and/or torsional) is the selected from among the natural frequencies identified by the analytical model. The natural frequency having an associated mode shape which exhibits significant localized bending at both the probable axial location of the crack and the site of response measurement of the shaft system, is chosen as the natural frequency of interest.

Figure 5B:
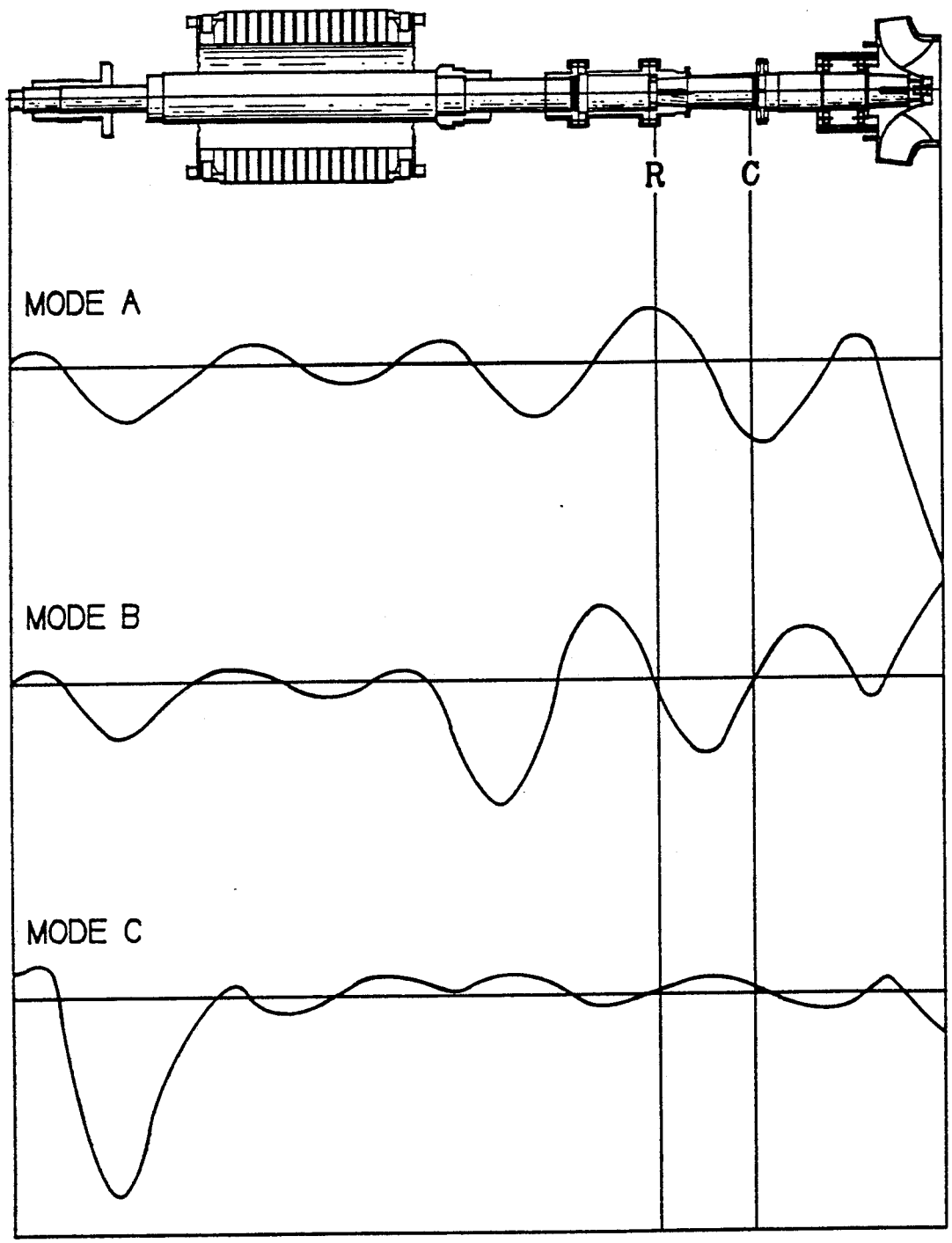
FIGS. 5b and 5c depict lateral mode shapes and torsional mode shapes, respectively, associated with various natural frequencies for an uncracked shaft system, as might be derived from the structural dynamics model.
Figure 5C:
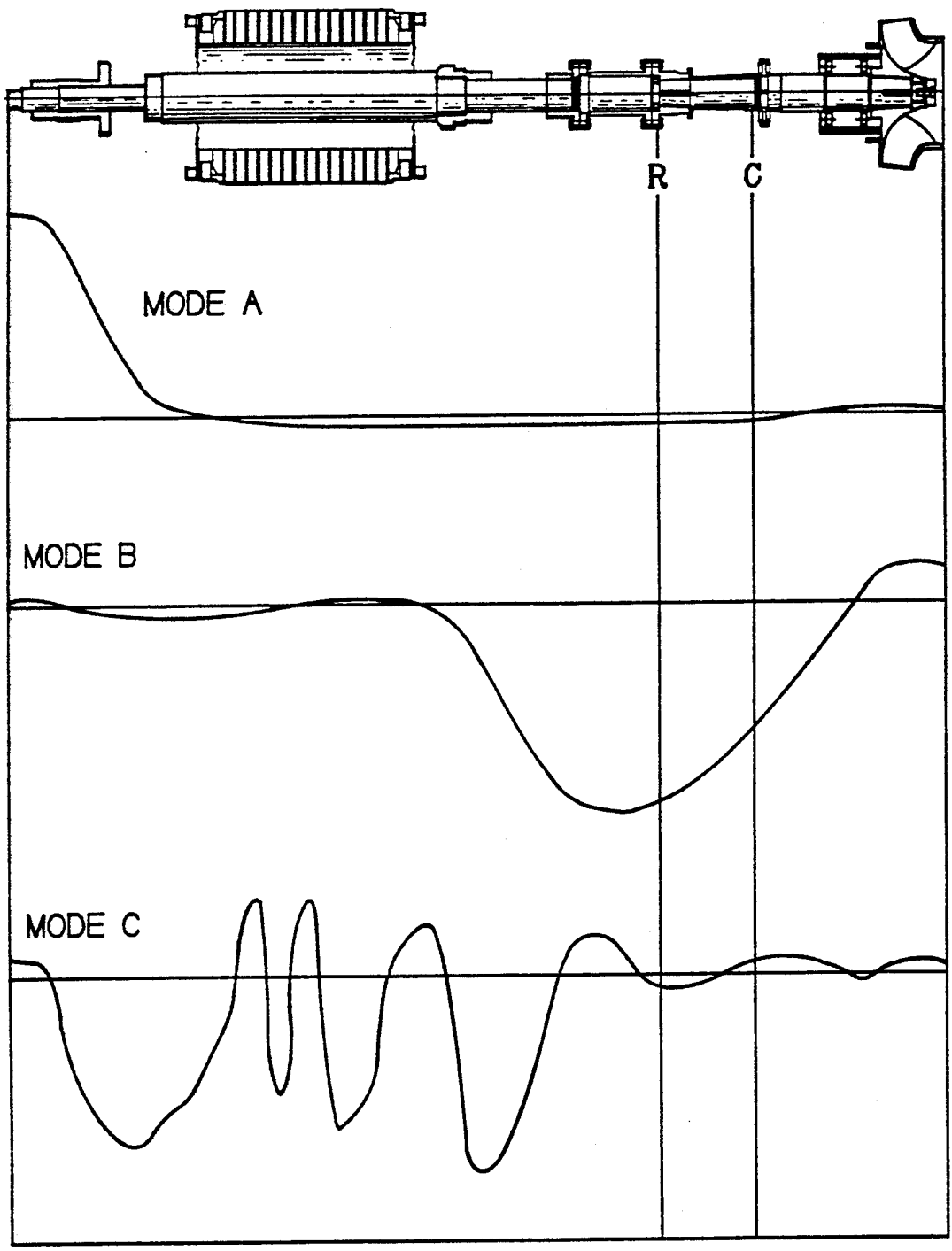

Sample mode shape curves are presented in FIGS. 5b and 5c and will now be described in order to explain how a natural frequency of interest can be selected. High local bending is characterized in the lateral mode shape curves (FIG. 5b) by a large change in the slope of the curve. In the torsional mode shape curves (FIG. 5c) high local bending is characterized by areas of high positive or negative slope, (i.e. high rate of change of angular twist). Lateral mode A in FIG. 5b is of interest for crack analysis due to the high bending, and high displacement at both the suspect crack location "c", and the response measurement site "R". Modes B, and C are not of interest because both the suspected crack and the response measurement sites are located at points of low bending and low deflection in both modes. Torsional mode B in FIG. 5c is of interest for crack analysis due to the high torsional bending at the suspected crack location "c" and the response measurement site "R". Modes A and C are not of interest because the angular displacement curves at the crack and response measurement sites do not show large slopes, therefore the bending is low at these points. The probable axial location of the crack also establishes the diameter D of the shaft for further study.

The new modal test method of the invention was developed so that a shaft system could be examined for a crack when access to the shaft was limited. The method enables regions of the shaft some distance from the response measurement point to be examined for cracks. This is accomplished by identifying a higher order natural frequency such that the mode selected has a region of high bending near the response measurement point and the suspected location of the crack.

Any position along the entire length of the shaft can be examined by using this technique. Each new position will require examining a different natural frequency and associated mode shape. Performing a natural frequency analysis of the shaft system allows for an analytical determination of the expected natural frequency of interest, mode shape and region of high bending in order to guide the experimental testing of the shaft system. The theory underlying the invention will now be briefly discussed.

The nature of a vibrating structure is such that it seeks the state of minimum potential energy. A structure undergoing vibration will dissipate energy through structural damping or hysteresis. It has been found that damping is encountered proportional to displacement but out of phase with the velocity of harmonic oscillation. This phenomenon can be described mathematically by:

$$[m]\ddot{u} + (1+ig)[K]\ddot{u} = B\sin Wt \tag{1}$$

where
"m" represents mass;
"ü" represents displacement coordinate;
"g" is the structural damping coefficient which is usually less than 0.05;
"K" represents shaft stiffness;
"B" represents the magnitude of the forcing function; and
"W" represents angular precession frequency.

The structural damping theory applies to the shaft crack detection method since it is the mechanism responsible for exciting orthogonal, closely spaced natural frequencies. The two orthogonal, primary modes of the cracked shaft correspond to directions perpendicular to and parallel to the crack "wave front" 84 (see the cross-sectional representation of an asymmetric shaft crack of FIG. 6), and these directions are referred to as the soft axis and stiff axis, respectively.

By exciting the shaft system from multiple radial directions, two lateral natural frequencies can be found which are slightly below the lateral natural frequency of interest measured for an uncracked shaft system. Their values with respect to circumferential position will indicate the location of the crack. Their frequency separation will be an indication of crack depth, a.

By exciting the shaft system in a tangential direction, a torsional natural frequency can be found which is slightly below the torsional natural frequency of interest measured for an uncracked shaft system. The frequency reduction will be an indication of crack depth, a.

Figure 7:
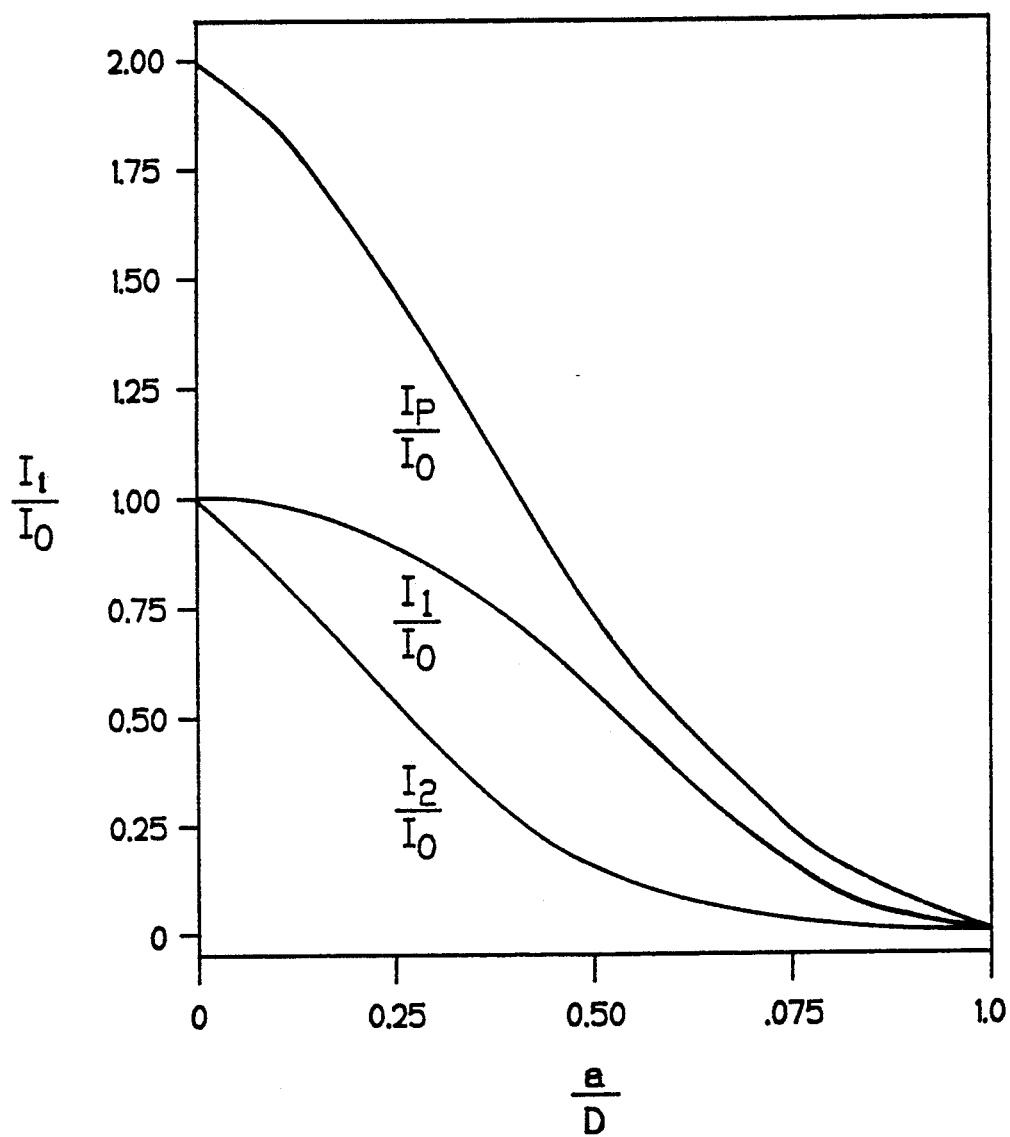
FIG. 7 is a plot of normalized diametrical and polar inertias along stiff, soft and polar axes as a function of crack ratio.

In accordance with the principals of the present invention, the analytical model of the uncracked shaft system is modified to include a representation of an asymmetric crack at the suspected axial location. The theoretical basis and a preferred approach for so modifying the analytical model will now be discussed. The first step in the preferred method of modeling a shaft crack is to calculate the normalized shaft section inertias for a range of crack depths. Inertia $I_1$ for the stiff direction and inertia $I_2$ for the soft direction are normalized using the inertia $I_0$ for the same diameter shaft uncracked. FIG. 7 depicts a plot of such normalized inertias as a function of crack ratio (crack depth a)/(shaft diameter D).

Figure 6:
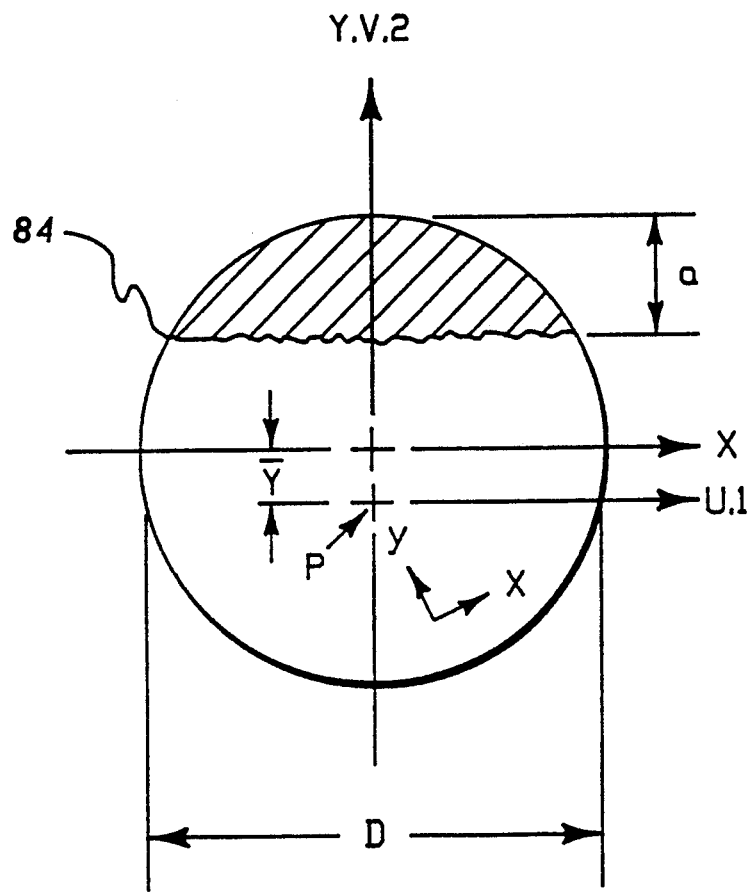
FIG. 6 is a cross-sectional view of an asymmetrically cracked shaft.

The stiffness of a shaft in both torsional and lateral modes is dependent on its section properties, referred to as area second moments or inertia. FIG. 6 depicts a cross section of a cracked shaft. The area inertias can be defined with respect to an arbitrary coordinate system [x,y] by the expressions:

$$I_x = \int y^2 dA \qquad (2)$$

$$I_y = \int X^2 dA \qquad (3)$$

$$I_{xy} = \int XY \, dA \qquad (4)$$

$$I_p = \int (X^2 + Y^2) dA = I_x + I_y \qquad (5)$$

The term $I_x$ relates to stiffness when bending the shaft about the x axis. Similarly, $I_y$ relates to bending the shaft about the y axis. $I_x$ and $I_y$ are always positive, but $I_{xy}$ can be positive, negative, or zero depending upon the orientation and position of the reference axes. $I_p$ relates to the stiffness when twisting about the z or polar axis. Refer to the shaft geometry defined in FIG. 6. Let the crack depth be called (a) and the diameter (D). Now construct coordinate system [X,Y] with its origin at the center of the circle representing the uncracked geometry. Rotate [X,Y] such that the Y-axis symmetrically bisects the crack. By definition, the term $I_{xy}$ will vanish if the cross section is symmetric about at least one axis. Therefore, the product of inertia with respect to the [X,Y] system vanishes, i.e. $I_{XY}=0$.

From classical beam theory and assuming small deflections, the shaft will bend about its neutral axis. For linear elastic analysis, the neutral axis coincides with the centroidal axis of the section.

As a crack propagates through a shaft, the section neutral axis will migrate in the direction of the crack wave front. At a given crack depth, (a), the neutral axis shifts to point P. A new set of coordinate axes is drawn parallel to [X,Y] and through P. This set of axes is referred to as the Primary Axes [U,V] for the given crack depth. Note that the section is still symmetrical about the V axis, so $I_{UV}=0$. The distance $\overline{Y}$ between the points 0 and P is defined as:

$$\overline{Y} = \int Y dA / dA \qquad (6)$$

evaluated over the internal region of the cracked section and with respect to [X,Y].

It is usual to refer to the principal values of section properties, which are the maximum and minimum possible values for $I_U$ and $I_V$, and where $I_{UV}$ must vanish. These properties are usually denoted as $I_1$ and $I_2$ where (with respect to [U,V]):

$$I_1 = \int V^2 dUdV \qquad (7)$$

$$I_2 = \int U^2 dUdV \qquad (8)$$

$$I_{12} = \int UV dUdV = 0 \qquad (9)$$

While the equations (7), (8), and (9) provide a precise mathematical definition of the Second Area Moments, evaluation of the integrals as defined can be tedious, even for the simple cracked shaft geometry. It can be show that the inertia terms with respect to a given set of axes can be evaluated with respect to a second set of axes:

$$I^{[UV]} = I^{[XY]} + Ad^2 \qquad (10)$$

where
$I^{[UV]}$ = Inertial components with respect to primary axes [UV] \qquad (11)

$I^{[XY]}$ = Inertial components with respect to centroidal axes [XY] \qquad (12)

where [X,Y] is parallel to [U,V]
A = Area of cross section
d = Distance between parallel axes (X,U) for $I_v$ or (Y,V) for $I_U$.
For the conditions shown in FIG. 6, (d) corresponds to the distance between the X and U axes, or:

$$d = \overline{Y} \qquad (13)$$

Now, it can be stated that the principal second moments are:

$$I_1 = I_U = I_X + A\overline{Y}^2 \qquad (14)$$

$$I_2 = I_V = + A(0)^2 = I_Y \qquad (15)$$

where:

$$I_X = \int Y^2 dXdY \qquad (16)$$

$$I_Y = \int X^2 dXdY \qquad (17)$$

It is still necessary to evaluate the expressions for $I_X$ and $I_Y$ on the domain by the cracked shaft. The above integrals can be solved using a summation of integrals over continuous subdomains:

$$I(X,Y) = I^1(X,Y) + I^2(X,Y) + I^3(X,Y) \quad (18)$$

where:

$$I^1(X, Y) = \int_{-R}^{-t} \int_{-W(X)}^{W(X)} (\xi) dY dX \quad (19)$$

$$I^2(X, Y) = \int_{-t}^{t} \int_{-W(X)}^{h} (\xi) dY dX \quad (20)$$

$$I^3(X, Y) = \int_{t}^{R} \int_{-W(X)}^{W(X)} (\xi) dY dX \text{ and,} \quad (21)$$

where:

$$W(x) = (R^2 - X^2); t = \sqrt{a(D-a)}; R = d/2; h = R - a$$

and $\xi = Y^2$ to evaluate $I_x$, or $\xi = X^2$ to evaluate $I_y$.

This technique, while mathematically precise is usually inconvenient. Therefore, a summation of components is used which states that:

$$I_x = \sum_i (Ix^i + A^i y_i^2) \quad (22)$$

$$I_y = \sum_i (Iy^i + A^i x_i^2) \quad (23)$$

where:

$Ix_i, Iy_i$ are second moments with respect to component centroids $A^i$ = area of component, positive or negative $x_i, y_i$ = distance from [X,Y] system to component's centroidal coordinate system.

In summary, the principal second moments for the cracked shaft are computed using the parallel axis theorem and method of components. The area and centroidal distances $Y_i$ change with varying crack depth necessitating many calculations. A computer program can be utilized to evaluate the expression over the range of interest. A map of three curves can be generated in dimensionless form to represent all cases. The results of these calculations are shown in FIG. 7.

The next step in the preferred manner of modeling the shaft crack is to calculate an equivalent right circular diameter $D_{eq}$ for each shaft section inertia in each respective direction, i.e. along the soft and stiff axes for lateral analysis and along the polar axis for torsional analysis in accordance with the following relationships:

$$D_{eqx} = \sqrt[4]{\frac{I_x \cdot 64}{\pi}} \quad (24)$$

$$D_{eqy} = \sqrt[4]{\frac{I_y \cdot 64}{\pi}} \quad (25)$$

$$D_{eqz} = \sqrt[4]{\frac{(I_x + I_y) \cdot 32}{\pi}} \quad (26)$$

An effective length L representing the axial extent of the shaft effected by the crack is then computed in accordance with the following formula:

$$L = 2(a)(\tan 53°) \quad (27)$$

Figure 8:
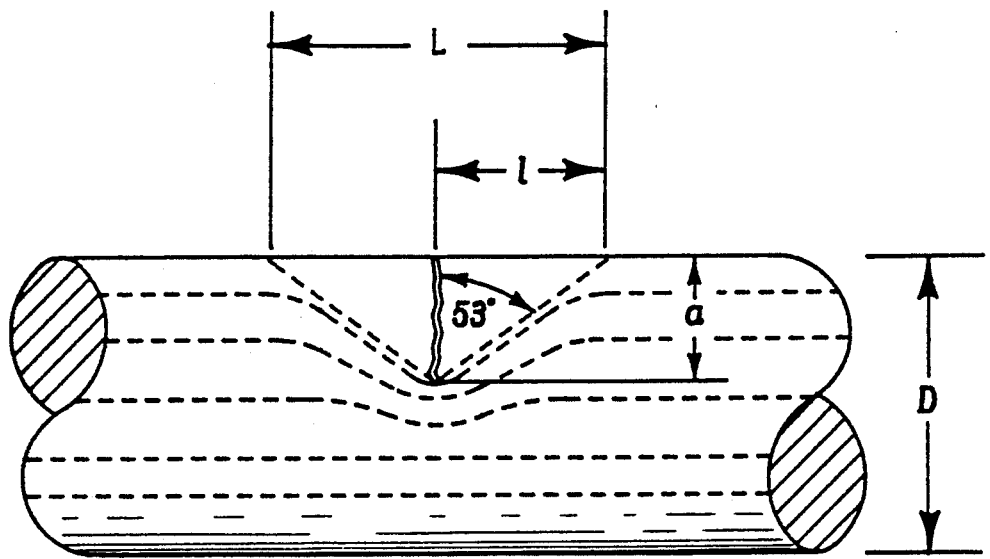
FIG. 8 is a schematic illustration of the lines of stress associated with a shaft crack and the dimensions used to calculate the effective length when modeling an asymmetric crack.

The effective length relationship is illustrated in FIG. 8, and the theory underlying this approach is described in a paper by B. Grabowski entitled "The Vibrational Behavior of a Turbine Rotor Containing a Transverse Crack", Transactions of the ASME Journal of Mechanical Design, Vol. 102, pp. 140-146, January 1980. A range of angles could be used to determine the effective length, but 53° appears to provide good results.

As shown in FIG. 8, lines of constant stress in the shaft are redirected due to the existence of the crack. An enhanced crack modeling approach which approximates the flow of stress through the shaft in the area of the crack will now be described with reference to FIGS. 8 and 8a. For a given crack ratio a/D, the shaft is remodeled over the effective crack length L. The remodeling includes calculating moments of inertia "I(new)$_i$" for each station "i" along the effective crack length according to equations 2, 3, and 5.

Each inertia for each station along the effective crack length is then replaced by a value "$I_i$" proportionate to its distance from the "C". $I_i$ being determined in accordance with the following equation:

$$I_i = I(old)_i - ((|(l_i - (L/2))/(L/2)| \cdot (I(old)_i - (I_l - I(new)_i)))$$

where $I(old)_i$ is a local inertia value of the shaft station "i" for an uncracked shaft, and $l_i$ is the local distance of the station "i" from the suspected crack location "C".

Figure 8A:
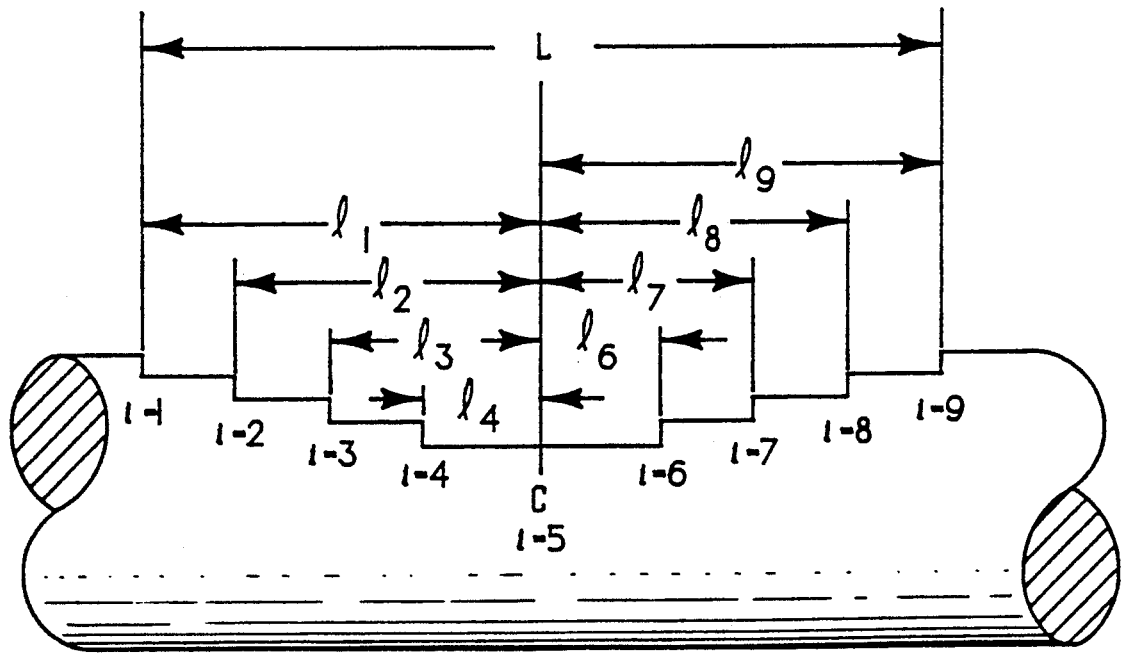
FIG. 8a is a schematic illustration useful in understanding an enhanced crack modeling feature of the present invention.

For the simple case of a right circular cylinder as shown in FIG. 8a, the above equation reduces to:

$$I_i = I_l - ((|l_i - (L/2))/(L/2)| \cdot (I_l - I_5))$$

When the crack modeling procedure is performed on a straight shaft, the moments of inertia $I_i$ represent those of a straight shaft with flat steps starting at a length $-L/2$ from the crack, increasing in depth until the suspected crack location is reached, then gradually stepping up to meet the original diameter at a length $+L/2$ from the crack location as shown in FIG. 8a.

The torque in a shaft element is given by:

$$T = \frac{\theta G I_p}{L} \quad (28)$$

where
$\theta$ is the angle of twist,
G is the shear modulus of elasticity,
L is the shaft element length, and
$I_p$ is the polar moment of inertia as defined by equation (5) above.

According to the classical theory of strength of materials, the terms on the right hand side of equation (28) other than $\theta$ are referred to as the torsional spring constant, K. Equation (28) may therefore be rewritten as:

$$T = K\theta$$

Hence, the asymmetric shaft properties combine to give a single torsional spring constant. One can observe that the torsional natural frequencies will exhibit downward shifts (but not splits) due to the asymmetric reduction in section properties $I_x$ and $I_y$.

The original structural dynamics model of the shaft system is modified at the suspected axial location of the crack using the equivalent diameter and effective length for the stiff and soft axes in the lateral analysis and for the polar axis in the torsional analysis, or the results of the enhanced crack modeling approach described above. From this modified model, the shaft system's new lateral and/or torsional natural frequencies and mode shapes for each direction, for a range of crack depths, can be derived and a plot of the new lateral and torsional natural frequencies as a function of crack ratio (a/D) made.

Figure 9:
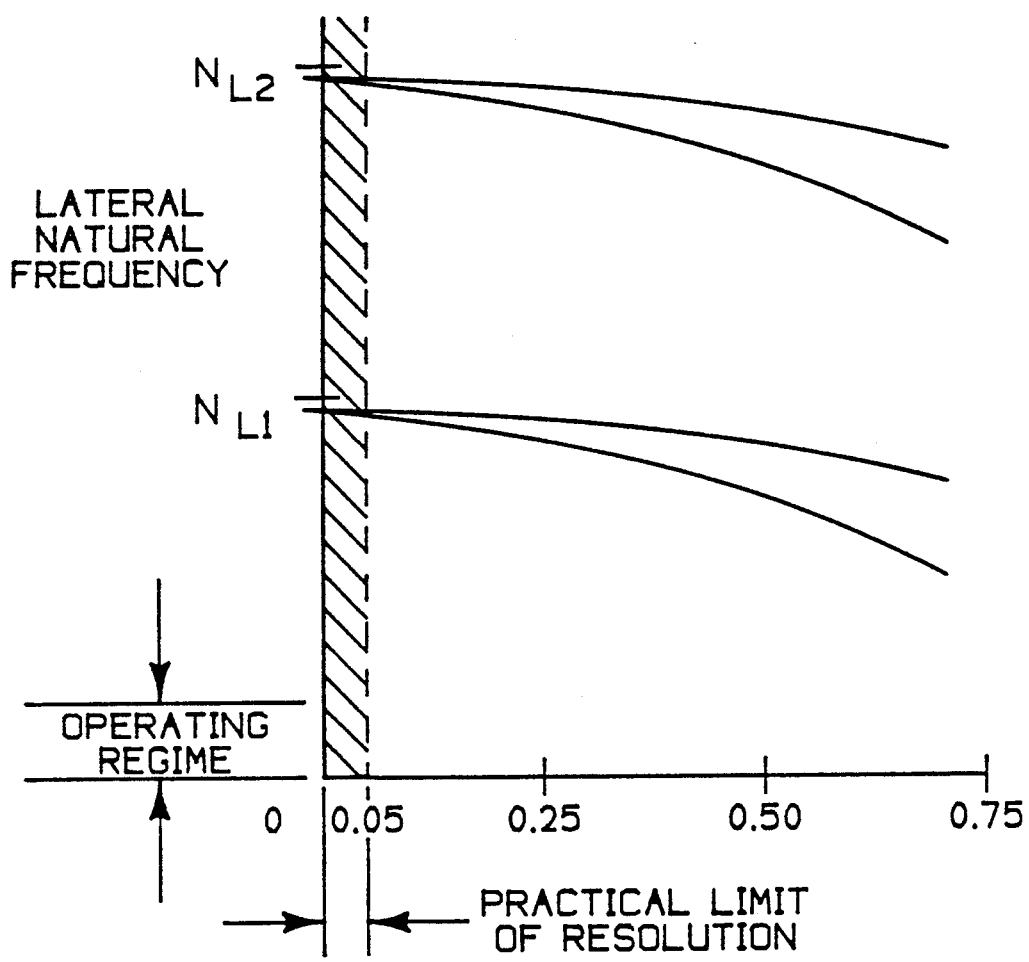
FIG. 9 is a plot illustrating the downward shift and split of shaft lateral natural frequencies as a function of crack ratio.

FIG. 9 presents such a plot for two lateral natural frequencies $N_{L1}$ and $N_{L2}$. The effect of the modeled crack on other lateral natural frequencies could similarly be plotted. Lateral natural frequencies for the uncracked shaft are plotted along the abscissa, and crack ratio is plotted along the ordinate in FIG. 9. As shown, the lateral natural frequencies are substantially higher than the operating regime of the RCP, as would be expected with a well designed machine. Cracks having a depth on the order of 5% or less of the local diameter are considered to be below the practical limit of resolution because of the lack of simultaneous mass and stiffness homogeneity in the real world. For example, a pair of keyways in the shaft will exhibit an asymmetry equivalent to a crack ratio of approximately, 0.03 which can be corrected for (i.e. subtracted out of the crack ratio parameter) to account for such known asymmetries in applying the present method. Beyond a crack ratio of 0.05, the map of FIG. 9 indicates the predicted split and shift of the lateral natural frequencies caused by the introduction of the crack in the model. As the severity of the crack increases, the spread between the two new frequencies becomes more pronounced. The calculated shift and split of a lateral natural frequency of interest for a particular suspected axial location of a crack, as derived from the modified model, can be correlated with actual lateral natural frequency measurements taken on the shaft system to determine the presence and size of a crack in the shaft.

Figure 10:
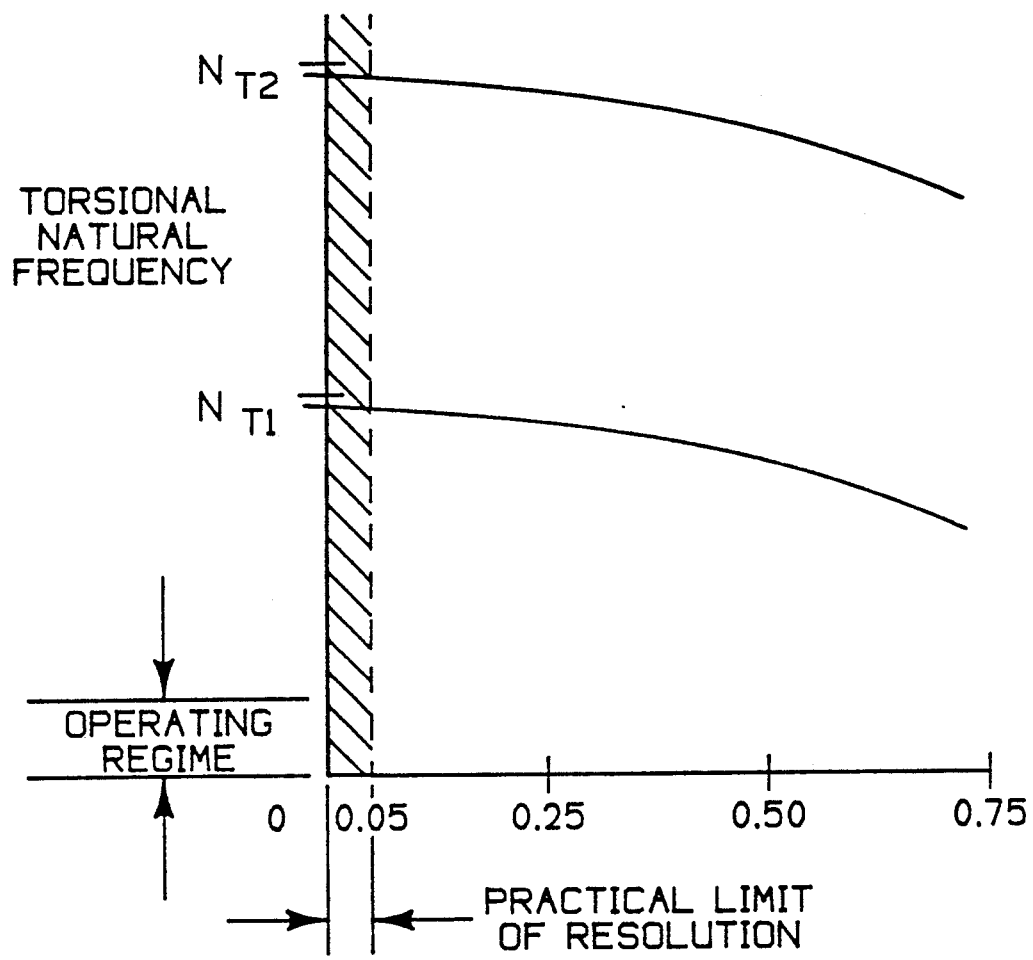
FIG. 10 is a plot illustrating the downward shift of shaft torsional natural frequencies as a function of crack ratio.
Figure 12:
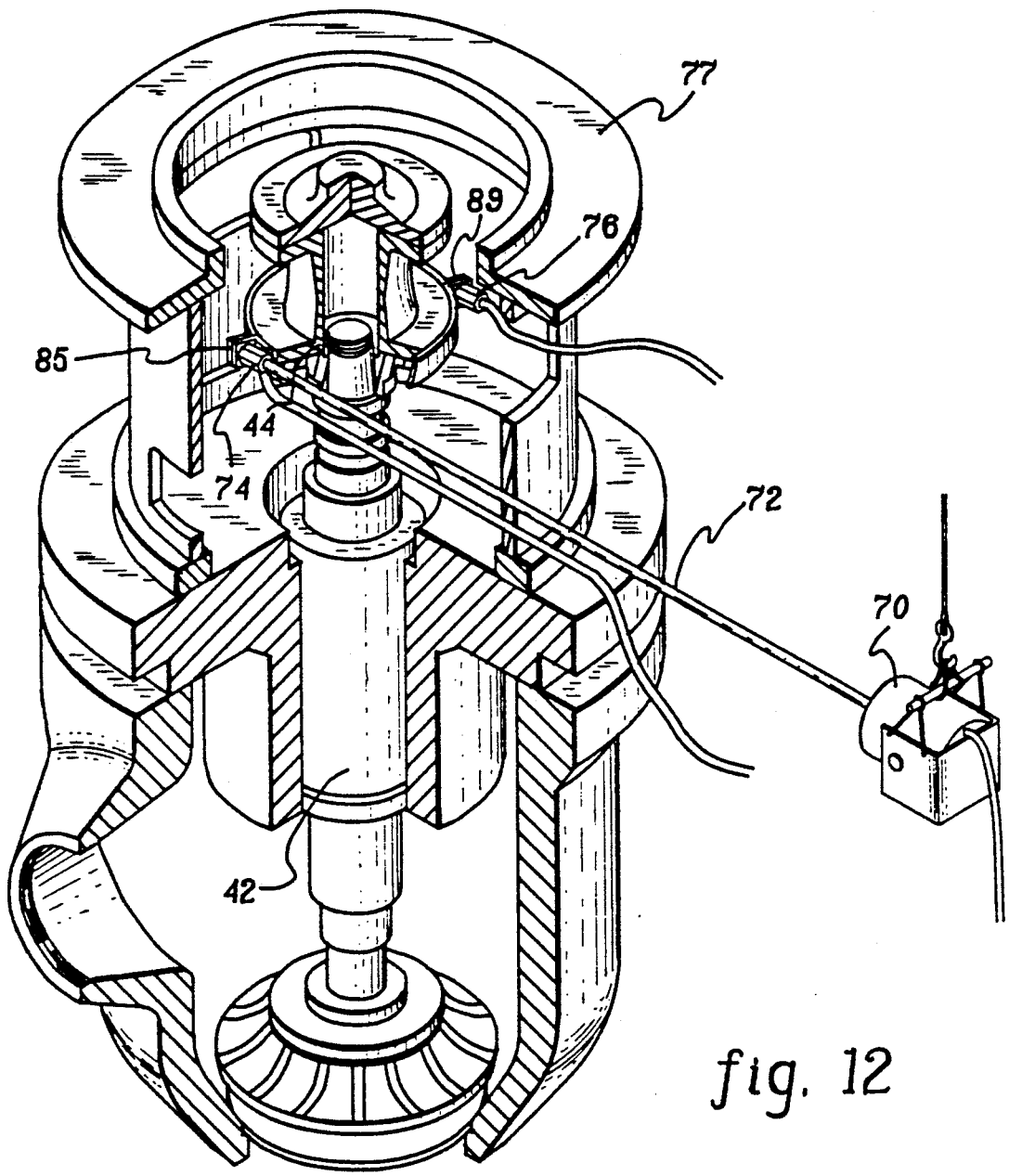
FIG. 12 is a partially cut-away sketch of an exemplary reactor coolant pump shaft torsional test instrumentation arrangement.

The map of FIG. 10 indicates the predicted shift of the torsional natural frequencies $N_{T1}$ and $N_{T2}$ caused by the introduction of the crack in the model. As the severity of the crack increases, the shift of the frequencies becomes more pronounced. The calculated shift of a torsional natural frequency of interest for a particular suspected axial location of a crack, as derived from the modified model, can be correlated with actual torsional natural frequency, measured as illustrated in FIG. 12, to determine the presence and size of a crack in the shaft.

Figure 11:
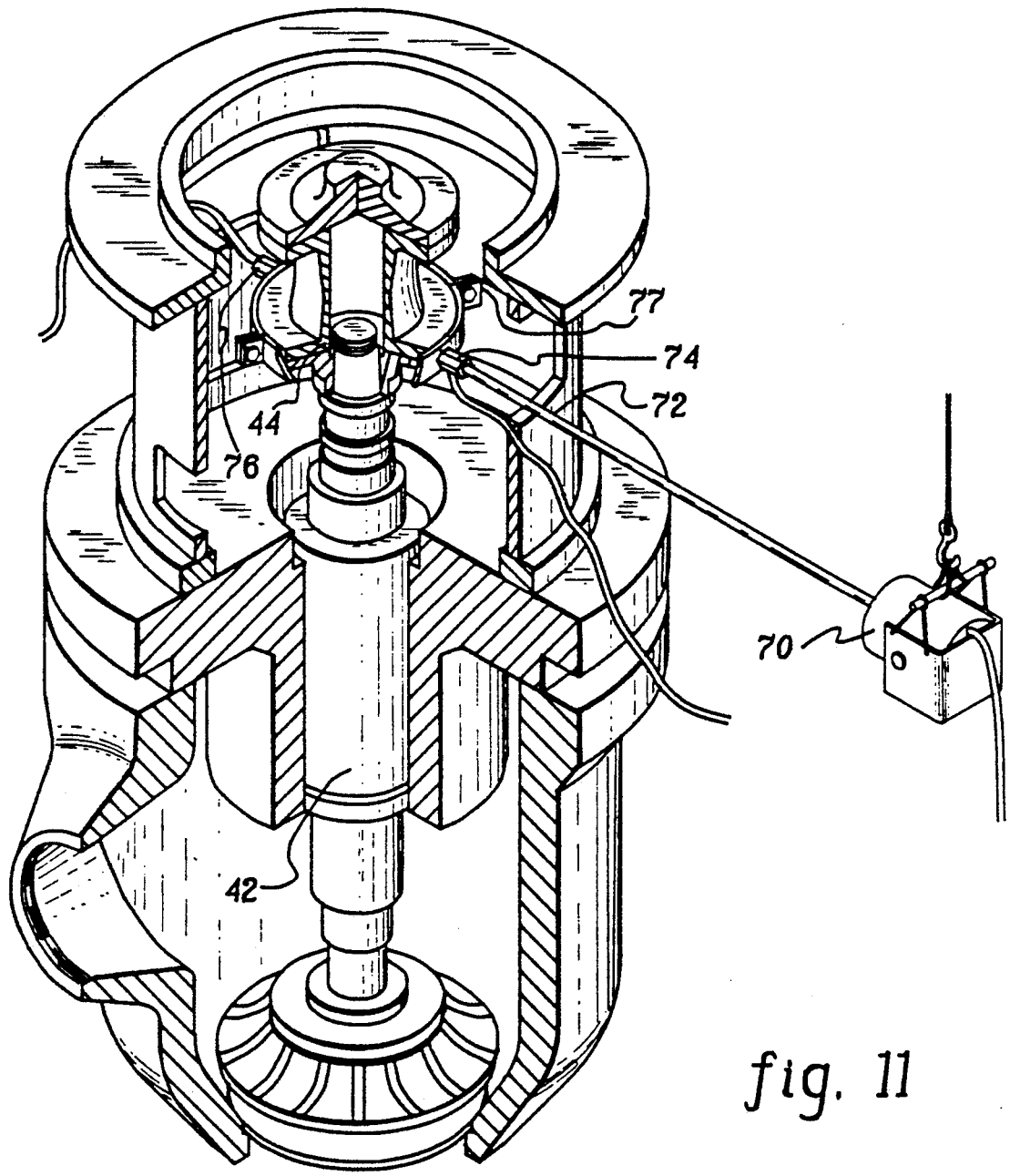
FIG. 11 is a partially cut-away sketch of an exemplary reactor coolant pump shaft lateral test instrumentation arrangement.

FIG. 11 illustrates exemplary test equipment which can be used to measure the actual lateral natural frequencies oft he shaft system of the RCP. The shaft system is excited radially using an electromagnetic shaker 70 connected to the coupling 44 by a stinger 72, i.e. a thin cylindrical rod. A load cell 74 measures the input force and provides an electrical signal representative thereof. The vibration response of the shaft system is preferably measured by an accelerometer 76 located diametrically opposite from the stinger 72. This 180 degree relationship is desirable since it maximizes resolution and avoids cross effects.

Figure 16A:
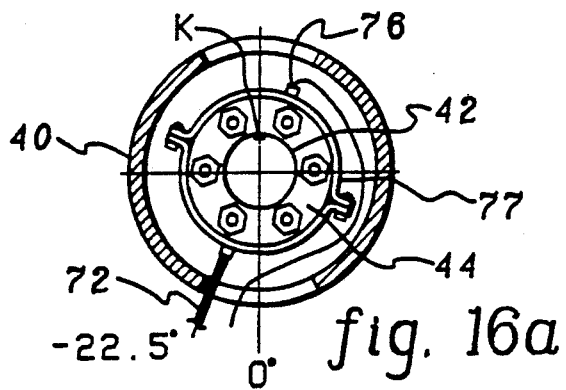
FIGS. 16a–16d are plan views illustrating a test instrument arrangement in which an instrumentation collar is repositioned about a shaft system under test.
Figure 17A:
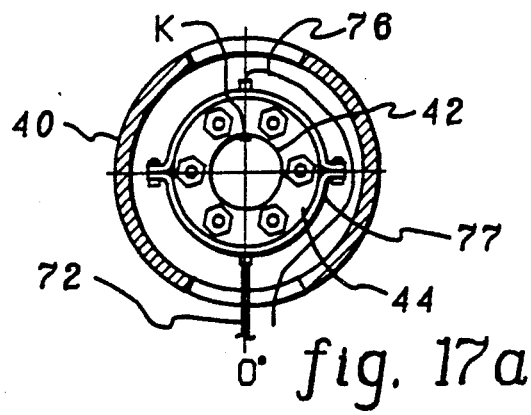
FIGS. 17a–17d are plan views depicting an alternative test instrumentation arrangement in which the shaft system under test is repositioned within a stationary collar.
Figure 16B:
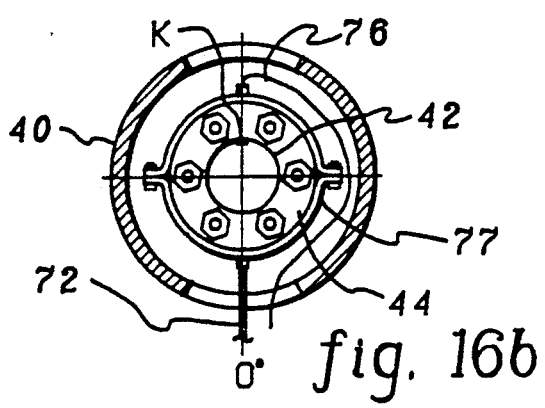
Figure 17B:
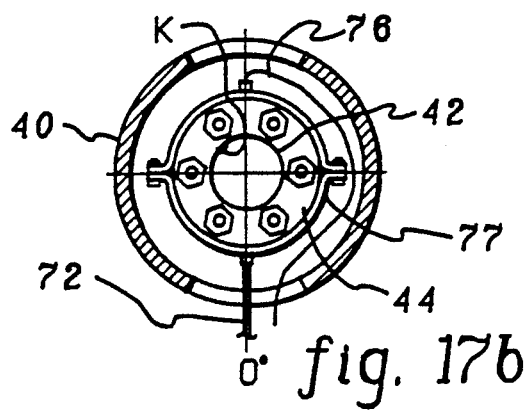
Figure 16C:
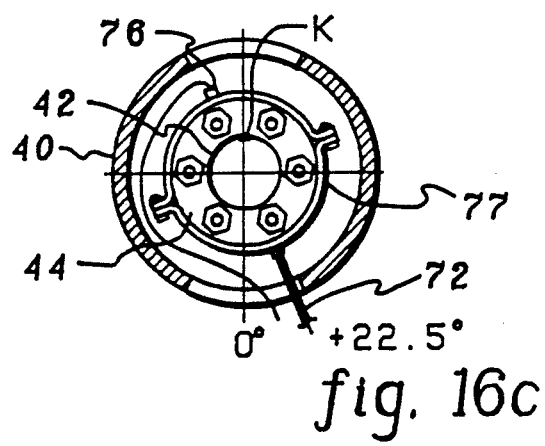
Figure 17C:
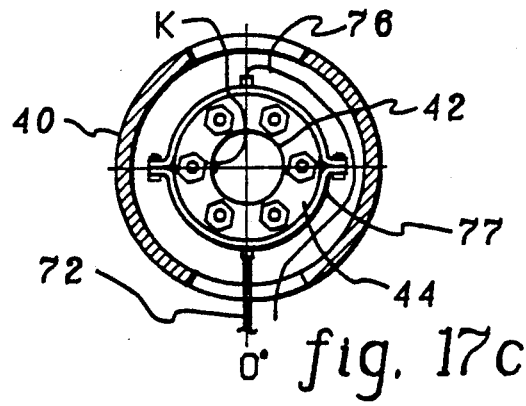

A rotatable collar 77, to which load cell 74 and accelerometer 76 can be attached, can be advantageously employed to quickly change the radial direction of measurement as illustrated in the respective views of FIGS. 16a, 16b, 16c. Alternatively, the position of collar 77 may remain constant and the shaft system can be controllably repositioned within the collar to take measurements along multiple selected radial directions, as illustrated in FIGS. 17a-17d. (In these figures, K indicates a shaft keyway.)

Figure 13:
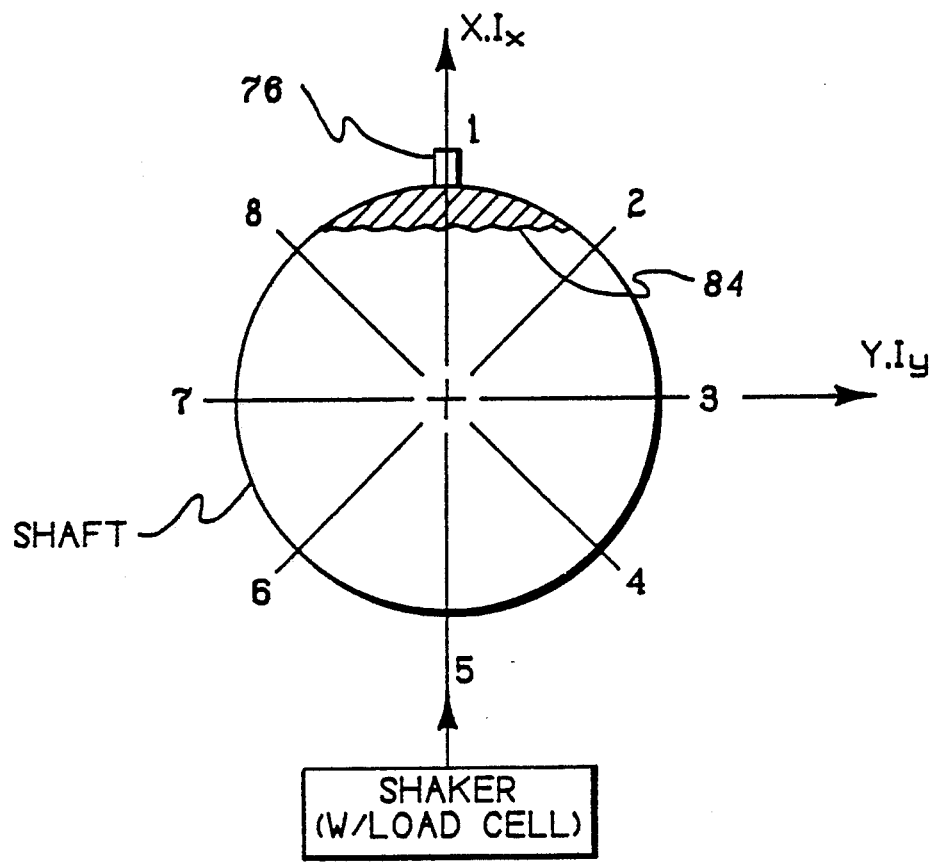
FIG. 13 illustrates how the lateral vibrational response measurements on the shaft are taken along multiple radial directions.
Figure 14:
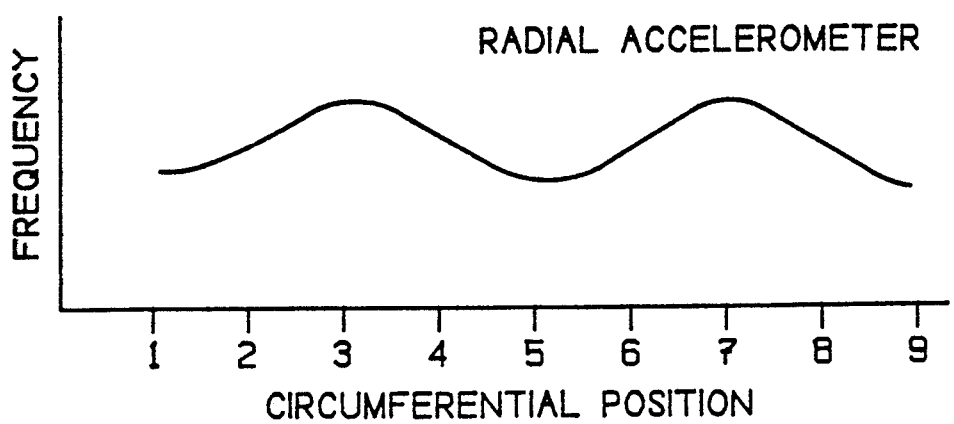
FIG. 14 is a plot of lateral natural frequency shift as a function of circumferential position.
Figure 15A:
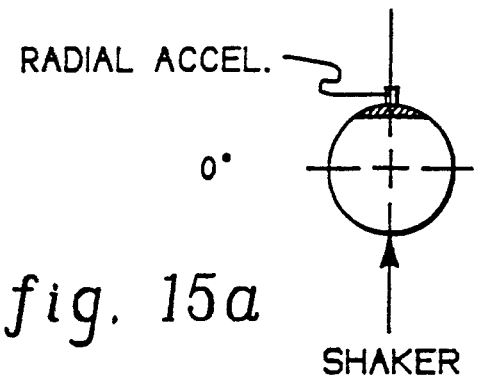
FIGS. 15a, 15c, 15e and 15g depict four radial directions of measurement
Figure 15B:
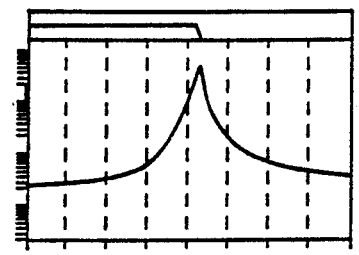
FIGS. 15b, 15d, 15f and 15h present a graph of natural frequency response function in a lateral analysis for a respective one of said four different radial directions.
Figure 15C:
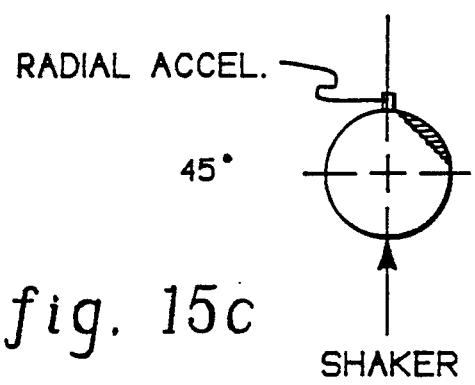
Figure 15D:
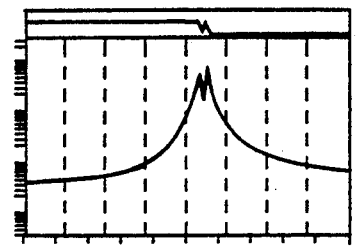
Figure 15E:
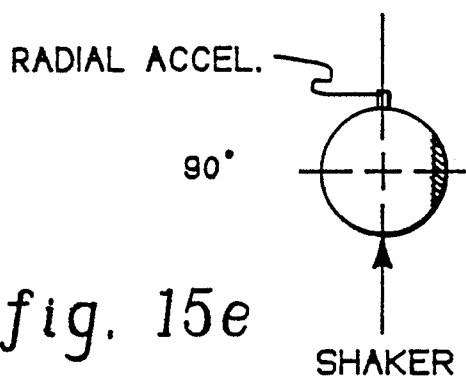
Figure 15F:
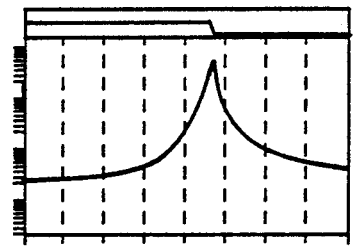
Figure 15G:
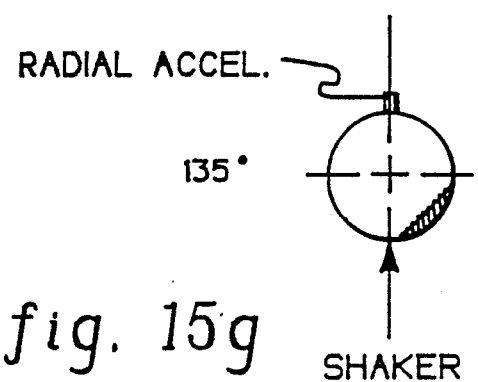
Figure 15H:
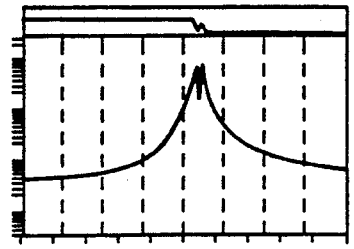

The output signals from accelerometer 76 and load cell 74 are fed through suitable couplers 86, 88 respectively, as shown in FIG. 4, to a FFT analyzer 78. The analyzer, in known fashion, provides a frequency response function, the peaks of which represent the actual natural frequencies. By exciting the shaft and measuring the system response in several predefined radial directions around the shaft (see FIG. 13), one can observe the variation of the shaft system lateral natural frequencies as a function of circumferential position (see FIGS. 14 and 15). In FIGS. 15a-15h, the graphs on the right side of the drawing sheet represent the frequency response function (FRF) for the associated angular direction illustrated on the left side of the sheet. Each peak in an FRF signifies a measured lateral natural frequency. At the 0° position (FIGS. 15a and 15b), the actual lateral natural frequency associated with the soft axis is exhibited. At the 90° position (FIGS. 15e and 15f), the measured lateral natural frequency associated with the stiff direction is presented. As would be expected, the lateral natural frequency in the stiff direction is somewhat higher than that in the soft direction. At intermediate angular positions (FIGS. 15c and 15d, 15g and 15h), both lateral natural frequencies are detected.

Referring again to FIG. 11, it will be seen that for a shaft of a RCP, a driving point modal analysis is employed (i.e. the input is applied and the output measured at the same axial location) because of the limited accessibility to the shaft. In other applications of the method of the present invention, the excitation site and response measuring position may be axially displaced.

Figure 16D:
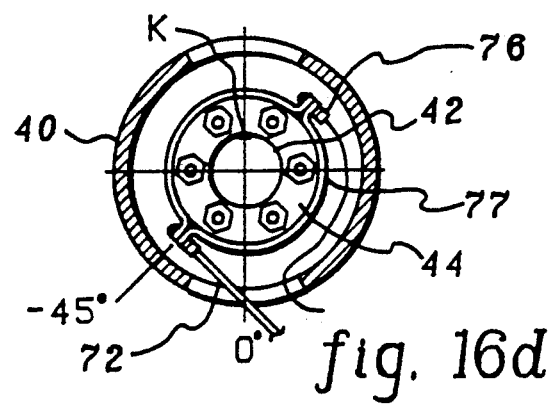
Figure 17D:
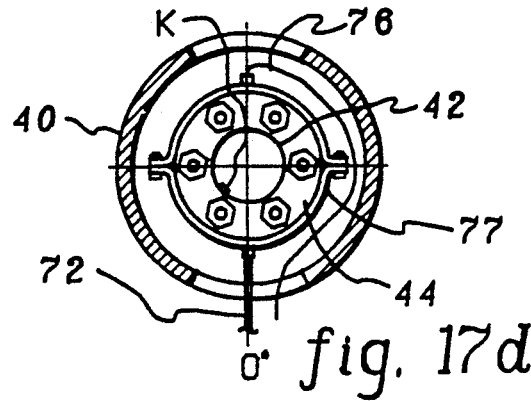

FIG. 12 depicts an exemplary test instrumentation arrangement for torsional analysis. As shown, a force excitation is applied through stinger 72 and load cell 74 to a first set of ears 85 on collar 77. Accelerometer 76 located on a diametrically opposed set of collar ears 89 measures the torsional vibrational response of the shaft system about its polar axis. The torsional excitation is thus applied along a tangential direction at a first location on the circumference of coupling 44 and the torsional response is measured along a tangential direction at a second circumferential location displaced 180 degrees from the first location (Ref. FIG. 16d). Signals from load cell 74 and accelerometer 76 are processed in a fashion identical to that earlier described for lateral analysis. In the torsional model only a single measurement reading is required to determine an actual natural frequency for comparison with the modified model predicted shift of a natural frequency of interest as a function of crack ratio.

Various known equipment can be used to implement the experimental portion of the method of the present invention. As an example, the following test equipment could be used to perform the cracked shaft modal testing:

1. A Zonic 6081Z Four Channel Analysis System With a Zoom Option, Signal Generator Option and Modal Analysis Software. The Zonic 6081Z multichannel FFT signal processor provides four channels for real time data acquisition with a 40 KHz signal range. The digital zoom analysis processor enables a 20u Hz frequency resolution. The system has a built in 15 megabyte Winchester disk drive and a 320 Kilobyte 3.5 inch micro floppy disk for data back up and storage. The signal generator option provides for user selectable wave forms with either linear or logarithmic sweep rates. Sine, Triangle, or Square wave forms can be selected from 1 Hz to 40 KHz. Random noise is possible from DC to 40 KHz. Programmable bursting of any wave form is selectable including band limited white noise. The burst noise output provides decreased test time and reduced leakage errors.

2. MB Dynamics Modal 50 Electromechanical Shaker With a model 2250 Power Amplifier. The MB Dynamics Modal 50 Electromechanical Shaker has been especially designed for modal testing. The shaker can be easily suspended for quick alignment with the test piece. The power amplifier model 2250 amplifies the input excitation signal from the Zonic Signal Generator to drive the shaker. An inertial mass can be attached to the suspended shaker to react against the excitation force.

3. Kistler Instrument Corporation 1 Volt/G Accelerometer (0.5 to 5000 Hz Range), 5516 Coupler; 9712 A50, 501b. force transducer, 99.2 mV/lb; 5120 coupler with DC offset adjustment for use with the force transducer.

By comparing the actual lateral and/or torsional natural frequencies in the regions of the lateral and/or torsional frequencies of interest with the new system frequencies predicted by the modified model (FIG. 9), the presence and severity (i.e. extent of cross sectional reduction as indicated by crack ratio) at the suspected axial location can be determined. Analysis of the FRFs at the various radial directions in the lateral analysis mode (see FIG. 15) reveals the circumferential location of the crack. Obviously, the test method can be employed in an iterative fashion to check for cracks at different axial locations. Similarly, the method, or just the experimental portion thereof, can be applied over time to monitor crack initiation and/or propagation.

Figure 18A:
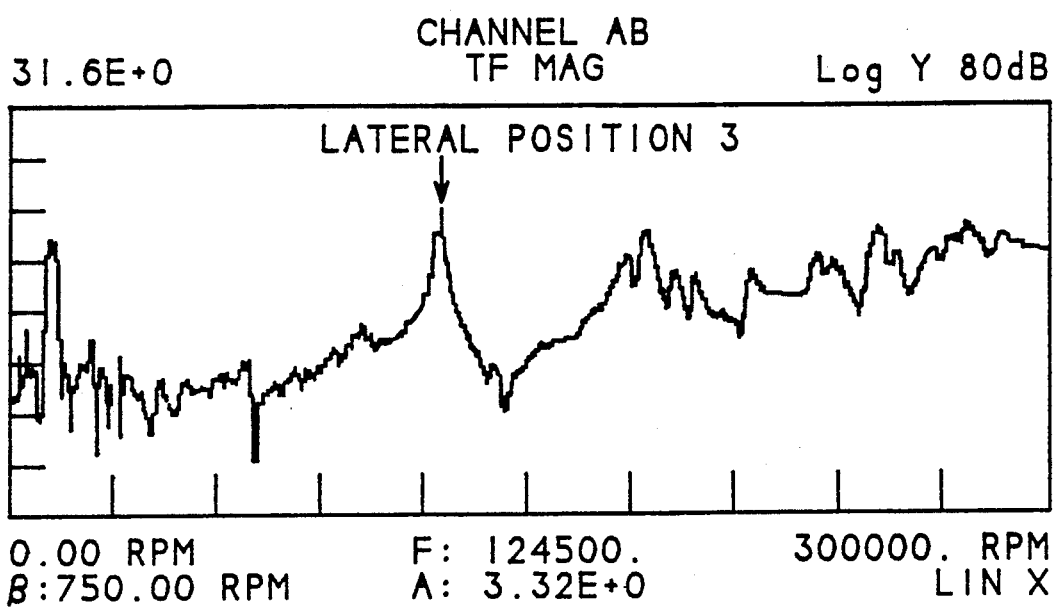
FIG. 18a is a plot showing an actual frequency response function measured in accordance with the method of the present invention.

FIG. 18a is a plot showing an actual frequency response function of a reactor recirculation pump shaft system measured utilizing the experimental portion of the method described herein. The peaks of the frequency response function indicate the measured lateral natural frequencies of the shaft system. The frequency response function is shown from 0 to 300,000 RPM. It is not obvious from this function which peak will be most effected by a crack at a given location. The analytical steps of the method of the present invention provide such guidance.

Figure 18B:
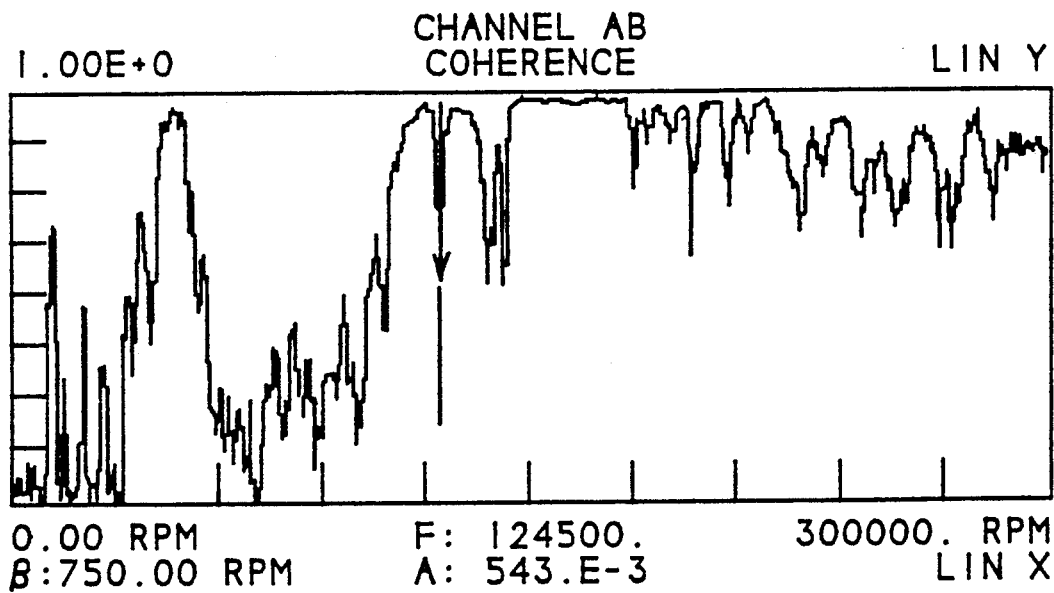

FIG. 18b is a plot showing an actual coherence function for the FRF shown in FIG. 18a. The coherence function enables one to gauge the cause/effect efficiency of the input to response of the natural frequencies of the structure under test. The coherence function ranges from 0 to 1. Typically, at a resonance the coherence should be very high (near 0.9). But if two closely spaced modes exist, the coherence will drop very low in the region of otherwise good data (see region "A" in FIG. 18b). This is a characteristic feature of closely spaced natural frequencies.

Figure 18C:
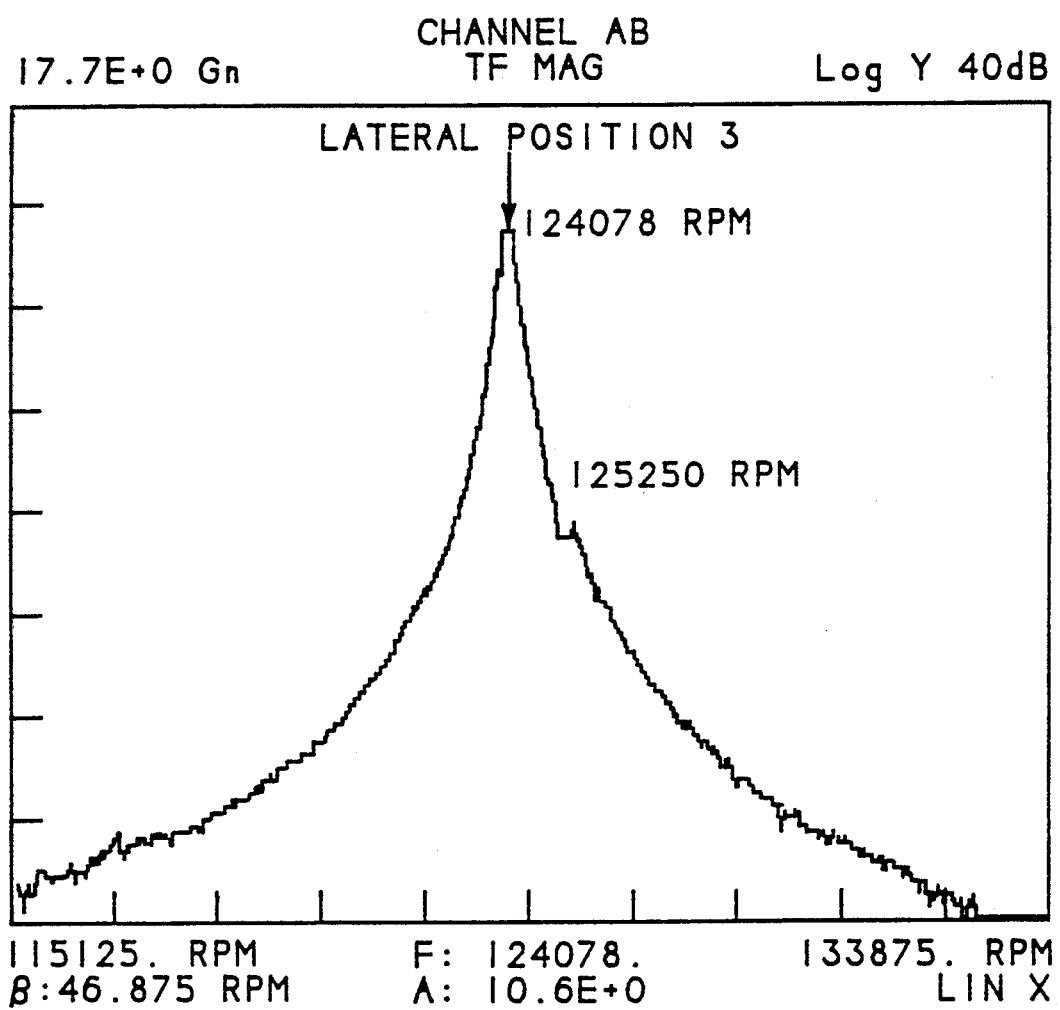

FIG. 18c is a plot showing a portion of FIG. 18a which has been expanded or zoomed to give much finer resolution of the peaks (natural frequencies). The natural frequency (F) of 124500 RPM has been replotted with the resolution ($\beta$) of the major peak enhanced ($\beta$ going from 750 RPM to 46.875 RPM, i.e. approximately 16 times finer examination). In FIG. 18c, a second peak can be seen on the upper shoulder of the main natural frequency of 124078 RPM, i.e. at 125250 RPM. Hence, the suggestion of closely spaced modes by the coherence function (FIG. 18b) is indeed correct.

Figure 18D:
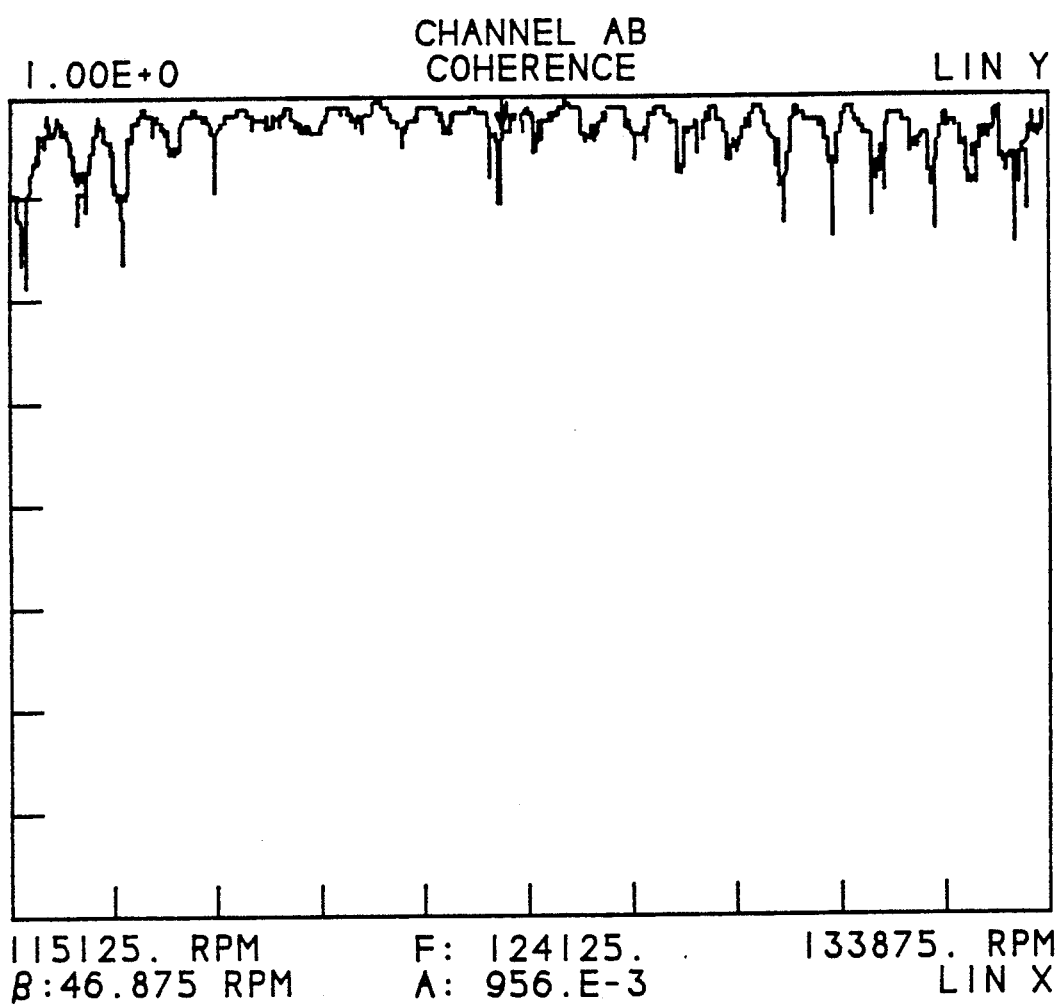
FIG. 18d is a plot of the coherence function for the expanded region of FIG. 18c.

FIG. 18d is a plot of the coherence function for the zoomed region of the FRF. One can see that the data is well above the 0.9 region across the plot. No indication of closely spaced modes exists because they are discreetly identified using the zoom feature of the analyzer. The actual data depicted in FIGS. 18a–d not only confirms the underlying method of the present invention, but also highlights the significance of the analytical portion thereof in interpreting the results of the experimental portion.

Figures 19, 19A:
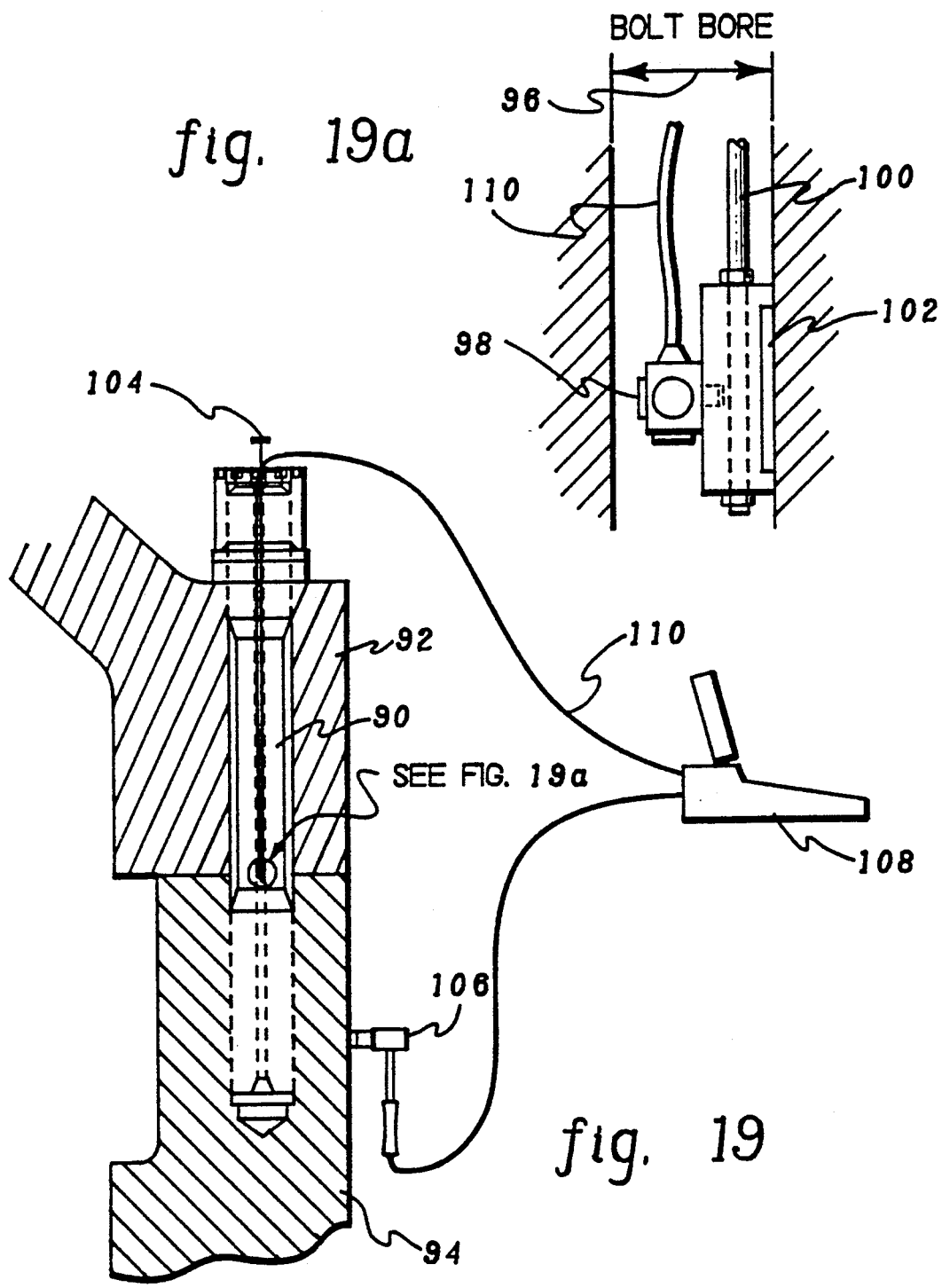
FIG. 19 schematically illustrates how the method of the present invention can be advantageously employed to detect a crack in a bolt that holds the cover on a nuclear reactor vessel.
FIG. 19a is a blown-up detailed view of a portion of FIG. 19.

The method of the present invention can be applied to shafts having orientations other than vertical (e.g. horizontal) and to structures other than rotors and rotatable shafts. FIGS. 19 and 19a illustrate application of the method to a bolt 90 used to secure a cover 92 to a reactor vessel base 94. The bolt contains an axially extending bore 96 in which an accelerometer 98 can be selectively located by a positioning rod 100 and secured by a magnet 102 at a suspected crack location. A positioning handle 104 connected to rod 100 facilitates positioning of the accelerometer 98 within the bore 96.

The bolt is excited to resonance by a hammer fitted with a force transducer 106 connected to FFT analyzer/computer 108. A vibration response measurement from accelerometer 98 is fed to FFT analyzer 108 via cable 110. The FFT analyzer can, in known fashion, indicate the actual natural frequencies of the bolt 90 in the region of a natural frequency of interest for comparison of these measured natural frequencies with predicted natural frequencies derived from a modified analytical model of the bolt in the manner hereinabove described.

A similar approach can be used to identify cracks in a horizontal turbine shaft having a central bore, and other similar structures. It is expected that the method can also be extended to detect cracks in bolts mounting an impeller to the bottom of a shaft of a RCP.

From the foregoing description, it will be apparent that a new method for detecting cracks in shafts has been developed which provides earlier detection than prior approaches. The new method allows for the identification of the presence, size and location of a crack anywhere along the shaft even when access to the shaft is limited. The method can be performed with the shaft at rest and is applicable to a wide variety of structures.

Although several presently preferred embodiments of the invention have been described and depicted, it will be apparent to those skilled in this art that various modifications, substitutions, additions, etc. can be made without departing from the spirit of the invention, the scope of which is defined by the claims appended hereto.

What is claimed is:

1. A method for detecting a crack in a shaft system under test, comprising the steps of:
   utilizing a multi-station structural dynamics model representative of the shaft system under test without cracks to derive natural frequencies of an uncracked shaft system, each natural frequency having an associated mode shape representative of shaft system deflection at the natural frequency of each point along a longitudinal axis of the shaft system;
   defining a probable axial location of a crack and selecting from among the natural frequencies derived from the model a natural frequency of interest having an associated mode shape which exhibits significant localized bending at said probable axial location of the crack and at a site of response measurement;

modifying the model to include a representation of a crack at said probable axial location;

employing said modified model to calculate effect of said representation of a crack upon the natural frequency of interest as a function of crack depth;

introducing an excitation force at an excitation site on the shaft system under test and taking measurement of vibrational response of the shaft system to said force at the site of response measurement;

processing said measurement to determine an actual natural frequency of the shaft system under test in a region near the natural frequency of interest; and comparing said actual natural frequency to the calculated effect of the representation of a crack upon the natural frequency of interest in order to determine the existence and severity of a crack in the shaft system under test.

2. The method of claim 1 wherein the modifying step comprises modifying the model to include a representation of an asymetric crack having a wave front extending parallel to a stiff axis and a crack depth extending along a soft axis; and wherein said step of employing the modified model to calculate the effect of the representation of a crack upon the natural frequency of interest comprises calculating a downward shift in the natural frequency of interest as a function of a ratio of crack depth to shaft diameter at said probable axial location.

3. The method of claim 2 wherein said model modifying step comprises representing said crack as a right circular section having an equivalent diameter for shaft section inertia for each of said soft axis and said stiff axis, and having an effective length.

4. The method of claim 3 wherein said modifying step comprises:

calculating the shaft section inertia for a range of crack depths at the probable axial location for the stiff axis and for the soft axis;

calculating an equivalent right circular diameter for each shaft section inertia along each of said axes, in accordance with the following equation:

$$D_{eq} = \sqrt[4]{\frac{I \cdot 64}{\pi}}$$

where "$D_{eq}$" represents the equivalent diameter of a right circular section for a specified axis, and "I" represents the shaft section inertia for a specified axis; and computing the effective length in accordance with the following equation:

$$L = 2(a)(\tan 53°)$$

where "L" represents the effective length and "a" represents the crack depth.

5. The method of claim 2 wherein said model modifying step comprises:

calculating moments of inertia $I(new)_i$ for each station i along an effective crack length according to the following equations:

$$I_x = \int y^2 dA$$

$$I_y = \int X^2 dA$$

$$I_p = \int (X^2 + Y^2) dA = I_x + I_y \text{ and}$$

calculating an inertia value $I_i$ for each station along the effective crack in accordance with the following equation:

$$I_i = I(old)_i - ((l_i - (L/2) \cdot (I(old)_i - I(new)_i))$$

where $I(old)_i$ is a local inertia value of the shaft section i for an uncracked shaft, and $l_i$ is the local distance of the station i from the probable axial location.

6. The method of claim 1 wherein said step of defining a probable axial location of a crack comprises identifying a shaft system location at which cracks tend to develop as a result of forces acting on the shaft system in accordance with an intended use of the shaft system.

7. The method of claim 1 wherein the step of taking measurement of vibrational response comprises measuring acceleration of the shaft system.

8. The method of claim 7 wherein acceleration is measured by an accelerometer, the excitation force is introduced by an electromagnetic shaker through a stinger and load cell, and wherein output signals from the accelerometer and load cell are provided to an FFT analyzer.

9. The method of claim 1 wherein the step of introducing an excitation force comprises imparting random white noise force excitation to the shaft system.

10. The method of claim 1 wherein the step of introducing an excitation force comprises imparting band limited vibrational energy in the region of the natural frequency of interest, to the shaft system.

11. The method of claim 1 wherein said processing step comprises determining a frequency response function with a fast Fourier transform analyzer.

12. The method of claim 11 wherein frequency resolution of the natural frequencies derived from the multi-station structural dynamics model of the shaft system is at least as great as frequency resolution of the fast Fourier transform analyzer.

13. The method of claim 1 wherein the distance between adjacent stations of the structural dynamics model is no greater than half the local shaft system radius.

14. The method of claim 1 wherein access to the shaft system under test is limited and the excitation force is introduced and the response measurement taken at the same axial location on the shaft system.

15. The method of claim 1 wherein the measurement of vibrational response is taken at a location which corresponds to the probable axial location of the crack.

16. The method of claim 1 further comprising the step of verifying the natural frequencies and associated mode shapes derived from the structural dynamics model by subjecting an actual shaft system to a roving force modal analysis.

17. The method of claim 1 further comprising the step of determining circumferential location of a crack in the shaft system under test by analyzing actual natural frequencies of the shaft system along multiple radial directions.

18. The method of claim 1 wherein the shaft system comprises a rotatable shaft system which is subjected to said excitation force while the shaft system is at rest.

19. The method of claim 1 wherein said shaft system has a hollow longitudinally extending central bore and the measurement of vibrational response is taken from within said bore.

20. The method of claim 19 wherein said shaft system comprises a bolt.

21. The method of claim 19 wherein said shaft system comprises a pipe.

22. The method of claim 1 wherein said excitation force produces a torsional excitation of the shaft system and said measurement comprises a measurement of torsional vibrational response.

23. The method of claim 22 wherein said excitation site and said site of response measurement are circumferentially displaced by 180 degrees.

24. The method of claim 23 wherein the modifying step comprises modifying the model to include a representation of an asymmetric crack having wave front extending parallel to a stiff axis and a crack depth extending along a soft axis; and wherein said step of employing the modified model to calculate the effect of the representation of a crack upon the natural frequency of interest comprises calculating a downward shift in the natural frequency of interest as a function of a ratio of crack depth to shaft diameter at said probable axial location.

25. The method of claim 24 wherein said model modifying step comprises representing said crack as a right circular section having an equivalent diameter for shaft section inertia for a polar axis extending longitudinally through the center of said shaft system, and having an effective length; and wherein said modifying step comprises:

calculating the shaft section inertia for a range of crack depths at the probable axial location for the stiff axis and for the soft axis;

calculating an equivalent right circular diameter for each shaft section inertia along the polar axis, in accordance with the following equation:

$$D_{eqz} = \sqrt[4]{\frac{(I_x + I_y) \cdot 32}{\pi}}$$

where "DeQ$_z$" represents the equivalent diameter of a right circular section for torsional analysis,
"Ix" represents the shaft section inertia for the stiff axis,
"Iy" represents the shaft section inertia for the soft axis, and
"Ip" represents the shaft polar moment of inertia; and
computing the effective length in accordance with the following equation:

$$L = 2(a)(\tan 53)$$

where "L" represents the effective length and
"a" represents the crack depth.

26. The method of claim 1 wherein the excitation force is introduced and the vibrational response is measured along a common diameter of the shaft system;

wherein the modifying step comprises modifying the model to include a representation of an asymmetric crack having a wave front extending parallel to a stiff axis and a crack depth extending along a soft axis; and wherein said step of employing the modified model to calculate the effect of the representation of a crack upon the natural frequency of interest comprises calculating a downward shift and a split in the natural frequency of interest as a function of a ratio of crack depth to shaft diameter at said probable axial location for lateral analysis.

27. The method of claim 26 wherein the excitation force is introduced and the vibrational response is measured along multiple diameters of the shaft system.

28. A method for detecting a crack in a shaft system under test, comprising the steps of:

employing a multi-station analytical model of the shaft system to determine a natural frequency of interest for a crack at a designated location and to predict a shift of said natural frequency of interest as a function of crack depth;

measuring an actual natural frequency of the shaft system under test at rest in response to a vibration inducing force excitation, said actual natural frequency being in the region of the natural frequency of interest; and comparing said actual natural frequency to the predicted shift of the natural frequency of interest to determine a correlation therebetween, whereby such a correlation indicates the existence of a crack in the shaft system and the severity thereof.

29. The method of claim 28 wherein the step of measuring an actual natural frequency of the shaft system comprises taking a measurement of vibrational response of the shaft system along a tangential direction.

30. The method of claim 29 wherein said force excitation is applied along a tangential direction at a first circumferential location on the shaft system, and measurement of vibrational response is taken along a tangential direction at a second circumferential location on the shaft system, said second circumferential location being displaced 180 degrees from the first circumferential location.

31. A method for detecting a crack in a shaft system under test, comprising the steps of:

(a) employing a multi-station analytical model of the shaft system to determine a first natural frequency of interest for a crack at a designated location and to predict a split and shift of said first natural frequency of interest as a function of crack depth for lateral analysis;

(b) measuring actual natural frequencies of the shaft system under test at rest in response to a lateral vibration inducing force excitation, said actual natural frequencies being in a region near the first natural frequency of interest;

(c) comparing said actual natural frequencies to the predicted split and shift of the first natural frequency of interest to determine a correlation therebetween;

(d) employing a multi-station analytical model of the shaft system to determine a second natural frequency of interest for the crack and to predict a downward shift of said second natural frequency of interest as a function of crack depth for torsional analysis;

(e) measuring an actual natural frequency of the shaft system under test at rest in response to a torsional vibration inducing force excitation, said actual natural frequency being in a region near the second natural frequency of interest; and (f) comparing said actual natural frequency to the predicted downward shift of the second natural frequency of interest to determine a correlation therebetween.

32. The method of claim 31 wherein the vibration including force excitation is applied and the actual natural frequencies are measured along a common shaft system diameter in step (b);
and wherein step (b) is performed along multiple shaft system diameters in order to determine circumferential location of a crack.

33. A method for detecting a crack in a shaft system under test, comprising the steps of:
introducing a force excitation at an excitation site on the shaft system under test;
measuring vibrational response of the shaft system to said excitation at a site of response measurement;
processing said measured vibrational response to determine an actual natural frequency of the shaft system under test in a region near a natural frequency of interest, said natural frequency of interest having been derived from a multi-station structural dynamics model representative of the shaft system under test without cracks, said natural frequency of interest having an associated mode shape which exhibits a region of high bending at a probable axial location of a crack and at the site of response measurement; and
comparing said actual natural frequency to one of (a) the natural frequency of interest and (b) an earlier similarly determined actual natural frequency of the shaft system, in order to identify the presence of a crack in said shaft system.

34. The method of claim 33 wherein said excitation is torsional; and further comprising the step of determining crack depth based upon a difference between the actual natural frequency of the shaft system and the natural frequency of interest.

35. The method of claim 34 wherein the step of determining crack depth comprises correlating said difference with a predicted shift of said natural frequency of interest as a function of crack depth.

36. The method of claim 35 wherein said predicted shift of said natural frequency of interest is derived from the multi-station structural dynamics model modified to include a representation of a crack at said probable axial location.

37. The method of claim 33 wherein said excitation is lateral; wherein said processing step comprises processing said measured vibrational response to determine a pair of actual natural frequencies of the shaft system under test in the region near the natural frequency of interest; and further comprising the step of determining crack depth based upon frequency differences between said pair of actual natural frequencies and between said pair of actual natural frequencies and the natural frequency of interest.

38. The method of claim 37 wherein said step of determining crack depth comprises correlating said pair of actual natural frequencies to a predicted shift and split in the natural frequency of interest as a function of crack depth.

39. The method of claim 38 wherein said predicted shift and split in the natural frequency of interest is derived from the multi-station structural dynamics model modified to include a representation of a crack at said probable axial location.

40. In a method for determining presence and severity of a crack in a shaft system under test, an improvement comprising the following sequence of steps:
utilizing a multi-station structural dynamics model representative of the shaft system under test without cracks to derive natural frequencies of an uncracked shaft system, each natural frequency having an associated mode shape representative of shaft system deflection at the natural frequency;
defining a probable axial location of a crack and selecting from among the natural frequencies derived from the model a natural frequency of interest having an associated mode shape which exhibits significant localized bending at said probable axial location of the crack and at a site of response measurement;
modifying the model to include a representation of a crack at said probable axial location; and
employing said modified model to calculate effect of said representation of a crack upon the natural frequency of interest as a function of crack depth, such that a measured actual natural frequency of the shaft system under test in a region of the natural frequency of interest can be compared to the calculated effect of the representation of the crack upon the natural frequency of interest in order to determine presence and severity of a crack in the shaft system under test.

41. A method for detecting a crack in a shaft system under test, comprising the steps of:
subjecting the shaft system to a vibration inducing force excitation at an excitation site;
measuring frequency response of the shaft system to said force excitation at a site of response measurement;
identifying in said frequency response an actual natural frequency in a region near a natural frequency of interest, said natural frequency of interest being derived from a multi-station structural dynamics model representative of the shaft system under test; and
comparing said actual natural frequency to the natural frequency of interest in order to determine the existence of a crack in the shaft system.

42. The method of claim 41 wherein said multi-station structural dynamics model is representative of the shaft system under test without cracks; and said natural frequency of interest has an associated mode shape which exhibits significant localized bending at a probable axial location of the crack and at the site of response measurement.

43. The method of claim 42 wherein said shaft system under test is at rest; said excitation is torsional; and said comparing step comprises determining a difference in frequency value between the actual natural frequency and the natural frequency of interest.

44. The method of claim 43 further comprising the step of correlating said difference with a predicted shift in the natural frequency of interest as a function of crack depth.

45. The method of claim 42 wherein said shaft system under test is at rest; the excitation is lateral; said identifying step comprises identifying a pair of actual natural frequencies near the natural frequency of interest; and said comparing step comprises determining differences in frequency value between said pair of actual natural frequencies and between said pair of actual natural frequencies and said natural frequency of interest.

46. The method of claim 45 further comprising the step of correlating said differences with a predicted shift and split of the natural frequency of interest as a function of crack depth.

* * * * *

UNITED STATES PATENT AND TRADEMARK OFFICE
CERTIFICATE OF CORRECTION

PATENT NO. : 5,068,800
DATED : November 26, 1991
INVENTOR(S) : Brook, et al.

It is certified that error appears in the above-identified patent and that said Letters Patent is hereby corrected as shown below:

Column 11, line 67, "L=2(a)(tan 53 )" should read "L=2(a)(tan 53°)".

Column 12, line 25, "$I_i=I(old)_i-(|(1_i-(L/2))/(L/2)|\cdot(I(old)_i-(I_1-I(new)_i))$" should read "$I_i=I(old)_i-(|(1_i-(L/2))/(L/2)|\cdot(I(old_i-I(new)_i))$".

Column 17, line 57, "L=2(a)(tan 53 )" should read "L=2(a)(tan 53°)".

Column 18, line 9, "$I_i=I(old)_i-((1_i-(L/2)\cdot(I(old)_i-I(new)_i))$ should read "$I_i=I(old)_i-(|(1_i-(L/2))/(L/2)|\cdot(I(old)_i-I(new)_i))$".

Column 19, line 45, "$DeQ_z$" should read "$D_{eqz}$".

Column 19, line 55, "L=2(a)(tan 53 )" should read "L=2(a)(tan 53°)"

Signed and Sealed this

Twenty-ninth Day of March, 1994

BRUCE LEHMAN

*Attest:*

*Attesting Officer*  Commissioner of Patents and Trademarks